(12) United States Patent
Novich et al.

(10) Patent No.: US 10,744,058 B2
(45) Date of Patent: Aug. 18, 2020

(54) METHOD AND SYSTEM FOR PROVIDING INFORMATION TO A USER

(71) Applicant: NeoSensory, Inc., Palo Alto, CA (US)

(72) Inventors: Scott Novich, Houston, TX (US);
David Eagleman, Palo Alto, CA (US);
Michael Vincent Perrotta, Palo Alto, CA (US)

(73) Assignee: NeoSensory, Inc., Houston, TX (US)

( * ) Notice: Subject to any disclaimer, the term of this patent is extended or adjusted under 35 U.S.C. 154(b) by 0 days.

(21) Appl. No.: 15/959,042

(22) Filed: Apr. 20, 2018

(65) Prior Publication Data

US 2018/0303702 A1 Oct. 25, 2018

Related U.S. Application Data

(60) Provisional application No. 62/487,832, filed on Apr. 20, 2017.

(51) Int. Cl.
| | |
|---|---|
| *A61H 3/06* | (2006.01) |
| *A61F 9/08* | (2006.01) |
| *G06K 9/00* | (2006.01) |
| *A61H 3/00* | (2006.01) |

(52) U.S. Cl.
CPC ............ *A61H 3/061* (2013.01); *A61F 9/08* (2013.01); *G06K 9/00671* (2013.01); *G06K 9/00677* (2013.01); *A61H 2003/001* (2013.01); *A61H 2003/007* (2013.01); *A61H 2003/063* (2013.01); *A61H 2201/165* (2013.01); *A61H 2201/1619* (2013.01)

(58) Field of Classification Search
None
See application file for complete search history.

(56) References Cited

U.S. PATENT DOCUMENTS

| | | |
|---|---|---|
| 3,342,923 A | 9/1967 | Henley |
| 4,665,494 A | 5/1987 | Tanaka et al. |
| 4,926,879 A | 5/1990 | Sevrain et al. |
| 5,553,148 A | 9/1996 | Werle |
| 5,655,271 A | 8/1997 | Maxwell-Trumble et al. |

(Continued)

FOREIGN PATENT DOCUMENTS

| | | |
|---|---|---|
| WO | 106698 | 9/2008 |
| WO | 069429 | 5/2012 |
| WO | 2012069429 A1 | 5/2012 |

OTHER PUBLICATIONS

Nakamura et al., An Actuator for the Tactile Vest—a Torso-Based Haptic Device, 2003, IEEE, 0-7695-1890-7/03 (Year: 2003).*

(Continued)

*Primary Examiner* — Carlos Garcia
(74) *Attorney, Agent, or Firm* — Jeffrey Schox; Caitlin Ploch

(57) ABSTRACT

A method for providing information to a user, preferably including: determining environmental information; determining a set of features based on the information; determining output parameters based on the features; and controlling a sensory output system to generate outputs based on the output parameters. A sensory output device, preferably including a plurality of sensory output actuators. A system for providing information to a user, preferably including one or more: sensory output devices, sensors, and computing systems.

14 Claims, 12 Drawing Sheets

(56) References Cited

U.S. PATENT DOCUMENTS

| | | |
|---|---|---|
| 6,027,463 A | 2/2000 | Moriyasu |
| 6,155,995 A | 12/2000 | Lin |
| 6,272,466 B1 | 8/2001 | Harada et al. |
| 6,295,703 B1 | 10/2001 | Adams et al. |
| 6,671,618 B2 | 12/2003 | Hoisko |
| 7,146,218 B2 | 12/2006 | Esteller et al. |
| 7,222,075 B2 | 5/2007 | Petrushin |
| 7,232,948 B2 | 6/2007 | Zhang |
| 7,921,069 B2 | 4/2011 | Canny et al. |
| 7,979,146 B2 | 7/2011 | Ullrich et al. |
| 8,005,681 B2 | 8/2011 | Hovestadt et al. |
| 8,068,025 B2 | 11/2011 | Devenyi et al. |
| 8,588,464 B2 | 11/2013 | Albertson et al. |
| 8,754,757 B1 | 6/2014 | Ullrich et al. |
| 8,952,888 B2 | 2/2015 | Van Den Eerenbeemd et al. |
| 9,019,087 B2 | 4/2015 | Bakircioglu et al. |
| 9,298,260 B2 | 3/2016 | Karaoguz et al. |
| 9,324,320 B1 | 4/2016 | Stolcke et al. |
| 9,345,433 B1 | 5/2016 | Shinozuka et al. |
| 9,443,410 B1 | 9/2016 | Constien |
| 9,474,683 B1 | 10/2016 | Mortimer et al. |
| 9,613,619 B2 | 4/2017 | Lev-Tov et al. |
| 9,626,845 B2 | 4/2017 | Eagleman et al. |
| 9,659,384 B2 | 5/2017 | Shaji et al. |
| 9,735,364 B2 | 8/2017 | Cheng et al. |
| 9,905,090 B2 | 2/2018 | Ullrich et al. |
| 9,987,962 B1 | 6/2018 | Salter et al. |
| 2002/0111737 A1 | 8/2002 | Hoisko |
| 2002/0194002 A1 | 12/2002 | Petrushin |
| 2003/0025595 A1 | 2/2003 | Langberg |
| 2003/0067440 A1 | 4/2003 | Rank |
| 2003/0117371 A1 | 6/2003 | Roberts et al. |
| 2003/0151597 A1 | 8/2003 | Roberts et al. |
| 2003/0158587 A1 | 8/2003 | Esteller et al. |
| 2005/0113167 A1 | 5/2005 | Buchner et al. |
| 2007/0041600 A1 | 2/2007 | Zachman |
| 2007/0242040 A1 | 10/2007 | Ullrich et al. |
| 2008/0120029 A1 | 5/2008 | Zelek et al. |
| 2008/0170118 A1 | 7/2008 | Albertson et al. |
| 2009/0006363 A1 | 1/2009 | Canny et al. |
| 2009/0012638 A1 | 1/2009 | Lou |
| 2009/0096632 A1 | 4/2009 | Ullrich et al. |
| 2010/0249637 A1 | 9/2010 | Walter et al. |
| 2010/0302033 A1 | 12/2010 | Devenyi et al. |
| 2011/0061017 A1 | 3/2011 | Ullrich et al. |
| 2011/0202155 A1 | 8/2011 | Ullrich et al. |
| 2011/0202337 A1 | 8/2011 | Fuchs et al. |
| 2011/0221694 A1 | 9/2011 | Karaoguz et al. |
| 2011/0319796 A1 | 12/2011 | Campdera |
| 2012/0023785 A1 | 2/2012 | Barnes et al. |
| 2013/0102937 A1 | 4/2013 | Ehrenreich et al. |
| 2013/0218456 A1* | 8/2013 | Zelek ............... G01C 21/3652 701/412 |
| 2013/0265286 A1 | 10/2013 | Da Costa et al. |
| 2014/0064516 A1 | 3/2014 | Cruz-Hernandez et al. |
| 2014/0363138 A1 | 12/2014 | Coviello et al. |
| 2015/0025895 A1 | 1/2015 | Schildbach |
| 2015/0038887 A1 | 2/2015 | Piccirillo |
| 2015/0070150 A1 | 3/2015 | Levesque et al. |
| 2015/0120289 A1 | 4/2015 | Lev-Tov et al. |
| 2015/0161995 A1 | 6/2015 | Sainath et al. |
| 2015/0227204 A1 | 8/2015 | Gipson et al. |
| 2015/0230524 A1 | 8/2015 | Stevens et al. |
| 2015/0272815 A1 | 10/2015 | Kitchens |
| 2015/0294597 A1* | 10/2015 | Rizzo ..................... A61H 3/04 340/4.12 |
| 2015/0305974 A1 | 10/2015 | Ehrenreich et al. |
| 2015/0351999 A1 | 12/2015 | Brouse |
| 2015/0356889 A1 | 12/2015 | Schwartz |
| 2016/0012688 A1 | 1/2016 | Eagleman et al. |
| 2016/0027338 A1 | 1/2016 | Ebeling et al. |
| 2016/0049915 A1 | 2/2016 | Wang et al. |
| 2016/0098844 A1 | 4/2016 | Shaji et al. |
| 2016/0098987 A1 | 4/2016 | Stolcke et al. |
| 2016/0103590 A1 | 4/2016 | Vu et al. |
| 2016/0187987 A1 | 6/2016 | Ullrich et al. |
| 2016/0254454 A1 | 9/2016 | Cheng et al. |
| 2016/0255944 A1* | 9/2016 | Baranski ............. A44C 5/0069 |
| 2016/0284189 A1 | 9/2016 | Constien |
| 2016/0292856 A1 | 10/2016 | Niemeijer et al. |
| 2016/0297611 A1 | 10/2016 | Williams et al. |
| 2016/0367190 A1 | 12/2016 | Vaitaitis |
| 2017/0206889 A1 | 7/2017 | Lev-Tov et al. |
| 2017/0213568 A1 | 7/2017 | Foshee |
| 2017/0290736 A1 | 10/2017 | Idris |
| 2017/0294086 A1 | 10/2017 | Kerdemelidis |
| 2017/0348184 A1 | 12/2017 | Pisharodi et al. |
| 2018/0284894 A1* | 10/2018 | Raut ..................... G06F 3/016 |
| 2018/0374264 A1* | 12/2018 | Gatson ..................... G01S 1/74 |
| 2019/0337451 A1* | 11/2019 | Bacchus ............... B60Q 9/008 |

OTHER PUBLICATIONS

Paneels et al., What's Around Me? Multi-Actuator Haptic Feedback on the Wrist, Apr. 14-18, 2013, IEEE, 978-1-4799-0088-6/13, pp. 407-412 (Year: 2013).*

Horvath et al., FingerSight: Fingertip Haptic Sensing of the Visual Environment, Mar. 6, 2014, IEEE, vol. 2, 2014 (Year: 2014).*

Jones et al., Development of a Tactile Vest, 2004, IEEE, 0-7695-2112-6/04 (Year: 2004).*

Tapson et al., The Feeling of Color: A Haptic Feedback Device for the Visually Disabled, 2008, IEEE, 978-1-4244-2879-3/08, pp. 381-384 (Year: 2008).*

Plant, Geoff, "Training in the use of the Tactaid VII: A case study", KTH Computer Science and Communication (STL-QPSR), 1994, vol. 35, No. 1, pp. 091-102.

* cited by examiner

METHOD AND SYSTEM FOR PROVIDING INFORMATION TO A USER

CROSS-REFERENCE TO RELATED APPLICATIONS

This application claims the benefit of U.S. Provisional Application Ser. No. 62/487,832, filed on 20 Apr. 2017, which is incorporated in its entirety by this reference.

TECHNICAL FIELD

This invention relates generally to the field of information delivery, and more specifically to a new and useful methods and systems for providing complex information through sensation, with multi-domain encodings.

BACKGROUND

Visual and auditory perception are important parts of an individual's ability to integrate into society, interact with objects in the environment, and perceive and respond to risks. Traditional devices for supporting individuals with vision impairments, hearing impairments, or other related conditions are deficient because they are highly invasive and require surgical implantation, risky (e.g., in terms of success rates, available only to certain demographics (e.g., age demographics), inconvenient to use, and/or expensive. Examples of such devices include retinal implants, vision correcting wearable devices, cochlear implants, and hearing aids. These deficiencies have motivated developments in technology areas associated with sensory substitution and/or sensory boosting, boosting of non-sight and/or non-auditory senses; however, such technologies are still limited in relation to how information from one sense can be encoded and processed using another sense (e.g., with respect to upsampling and downsampling issues), density of information that can be processed and encoded, cost, ease of use, and adoption by users.

Thus, there is a need in the field of information delivery for a new and useful method and system for providing complex information. This invention provides such a new and useful method and system.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Overview

Figure 1:
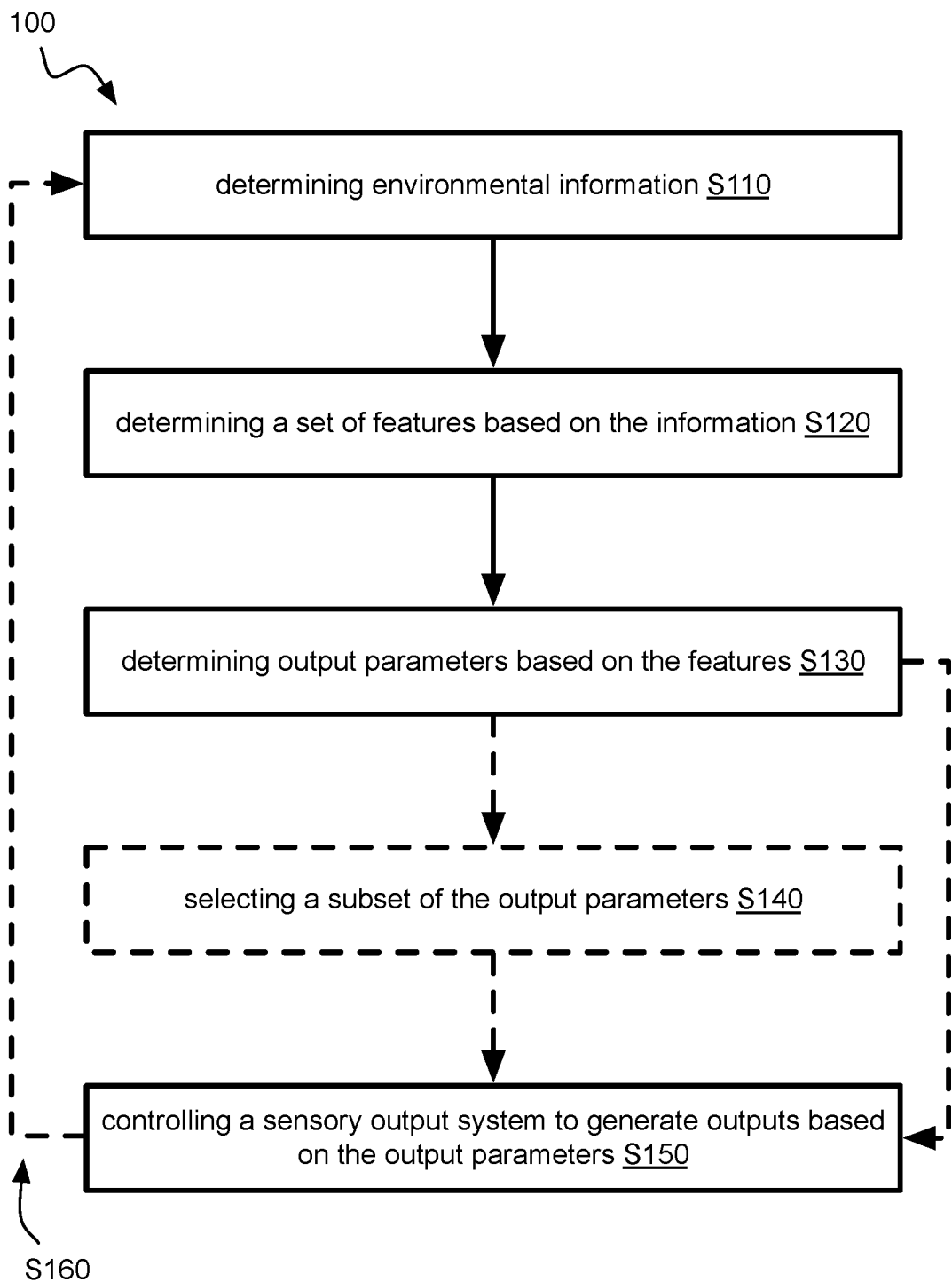
FIG. 1 depicts a schematic of a method for providing information to a user.

A method 100 for providing information to a user preferably includes (e.g., as shown in FIGS. 1 and/or 2): determining environmental information in Block S110 (e.g., information associated with an environment of a user); determining a set of features based on the information in Block S120; determining output parameters based on the features in Block S130; and controlling a sensory output system (e.g., tactile output device) to generate outputs based on the output parameters in Block S150. The method 100 can optionally include: selecting a subset of the output parameters in Block S140 (e.g., wherein only outputs based on the selected subset are generated in Block S150); repeating any or all of Blocks S110-S150 in Block S160; and/or any other suitable Blocks.

Figure 5:
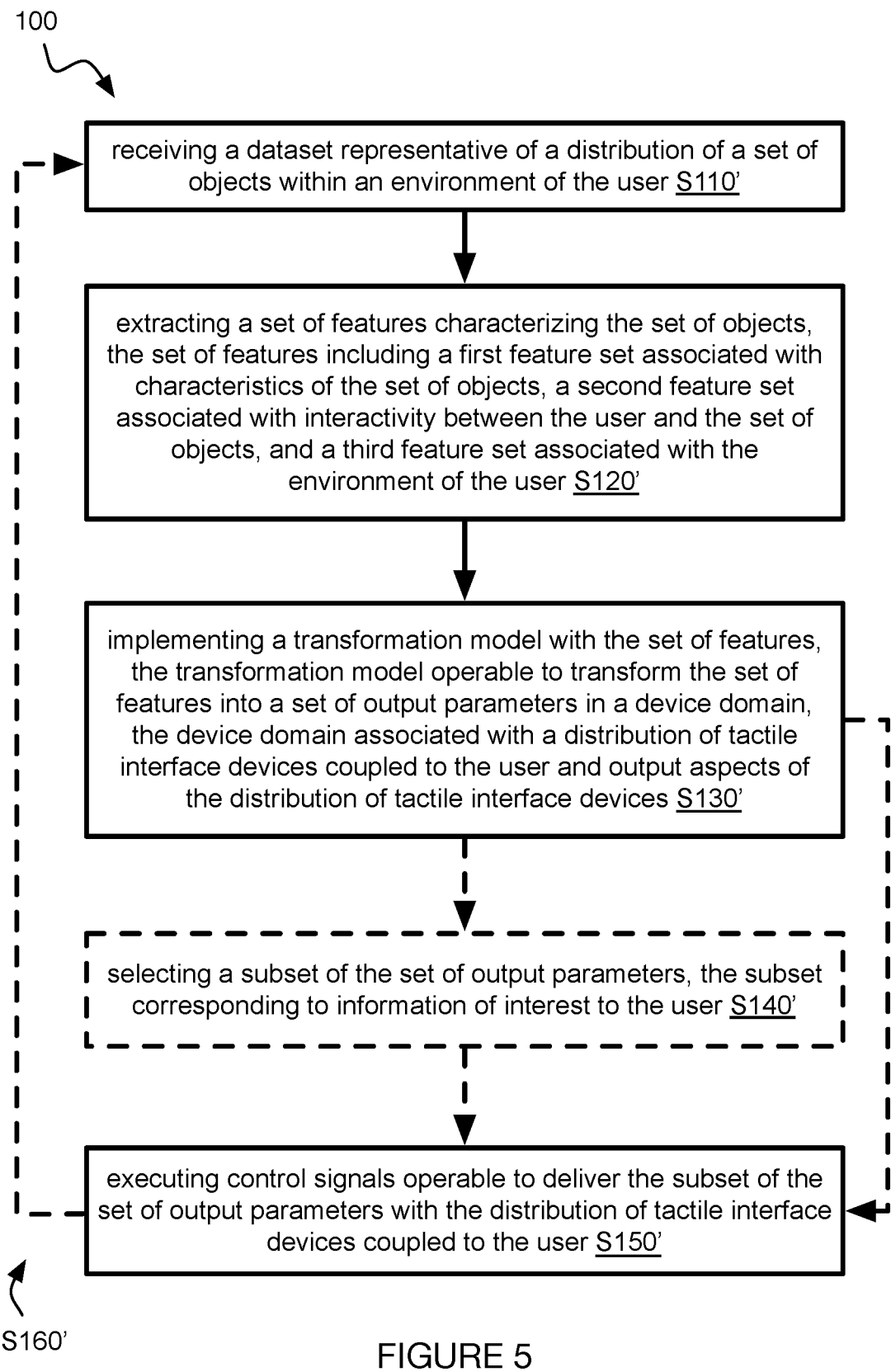
FIG. 5 depicts a schematic of an embodiment of the method.

For example, an embodiment of the method 100 includes (e.g., as shown in FIG. 5): receiving a dataset representative of a distribution of a set of objects within an environment of the user S110'; extracting a set of features characterizing the set of objects, the set of features including a first feature set associated with characteristics of the set of objects, a second feature set associated with interactivity between the user and the set of objects, and a third feature set associated with the environment of the user S120'; implementing a transformation model with the set of features, the transformation model operable to transform the set of features into a set of output parameters in a device domain, the device domain associated with a distribution of tactile interface devices coupled to the user and output aspects of the distribution of tactile interface devices S130'; selecting a subset of the set of output parameters, the subset corresponding to information of interest to the user S140'; executing control signals operable to deliver the subset of the set of output parameters with the distribution of tactile interface devices coupled to the user S150'; and/or repeating Blocks S110'-S150', as the user moves about the environment S160'.

The method 100 preferably functions to implement multi-domain encodings that map device outputs (e.g., provided stimuli) to higher-dimensional representations (e.g., of vision, in relation to objects in an environment of a user). As such, the method 100 can allow a user who is impaired in one or more senses to receive information that would otherwise be received through the one or more senses. The method 100 can thus operate to provide a means for sensory substitution and/or sensory boosting to allow a user to receive and process information. The method 100 can, however, additionally or alternatively be used for users who are not impaired in one or more senses, but for whom receiving of information from multiple sensory sources is desired. The method 100 preferably provides information to impaired users through touch sensation, However, the method 100 can additionally or alternatively implement any other suitable sensory substitution or sensory boosting regime. In specific applications, the method 100 can operate to allow a user with vision impairment, hearing impairment, and/or other forms of impairment to move about his/her environment without other guidance, using a tactile output system (e.g., wearable tactile output device device) including a distribution of haptic interface devices (e.g., haptic actuators).

The method 100 can thus be implemented using system components described in more detail below, and/or using one or more embodiments, variations, and/or examples of the system described in U.S. application Ser. No. 14/750, 626, titled "Providing Information to a User Through Somatosensory Feedback" and filed on 25 Jun. 2015, which is herein incorporated in its entirety by this reference. However, the method 100 can additionally or alternatively be implemented using any other suitable system or system components for providing information to users through feedback devices.

2. System

The system preferably includes one or more sensory output devices (e.g., tactile output devices, such as devices including an array of haptic actuators), which are preferably configured to provide sensory stimuli to a user, and can additionally or alternatively include one or more sensors, identifiers (e.g., tags), computing systems, and/or any other suitable elements. The sensory output devices preferably include a plurality of sensory output actuators, and can additionally or alternatively include one or more communication modules, power modules, computation modules (e.g., processors, memory, etc.), housings (e.g., enclosing and/or affixing other elements of the device, configured to mechanically couple the device to a user, etc.), and/or any other suitable elements.

The sensors can include local sensors (e.g., sensing an environment of the device and/or user; sensors located and/or sensing regions within a threshold distance of the sensory output device and/or user, such as 0.1 m, 0.3 m, 1 m, 2 m, 5 m, 10 m, 20 m, 50 m, 100 m, 200 m, 0.1-1 m, 1-10 m, 10-100 m, 100-1000 m, etc.), remote sensors (e.g., sensing a separate environment; sensors located and/or sensing regions farther than a threshold distance of the sensory output device and/or user, such as 10 m, 20 m, 50 m, 100 m, 200 m, 500 m, 1 km, 10 km, 10-100 m, 100-1000 m, 1-10 km, 10-1000 km, etc.), virtual inputs (e.g., associated with a virtual environment), and/or any other suitable sensors in any other suitable configuration. The local sensors can include, for example, sensors of (e.g., integrated into, attached to, etc.) the sensory output device, other sensors associated with the user (e.g., sensors of an electronic user device, such as a smartphone or tablet), and/or sensors associated with the environment (e.g., sensors integrated into and/or attached to a building or outdoor area, such as sensors arranged within every city block of an urban region). The remote sensors can include, for example, sensors associated with other people (e.g., sensors of other people's electronic user devices and/or sensory output device) and/or sensors associated with other environments. However, the sensors can additionally or alternatively include any other suitable sensors in any other suitable locations.

The sensors can include, for example, one or more: cameras (e.g., CCD, CMOS, multispectral, visual range, hyperspectral, stereoscopic, etc.), time of flight (ToF) sensors (e.g., lidar, radar, sonar, optical rangefinder, etc.), spatial sensors (e.g., inertial measurement sensors, accelerometer, gyroscope, altimeter, magnetometer, etc.), location sensors (e.g., GPS, GNSS, triangulation, trilateration, etc.), audio sensors (e.g., transducer, microphone, etc.), barometers, light sensors, temperature sensors, current sensors (e.g., Hall effect sensor), air flow meters, voltmeters, touch sensors (e.g., resistive, capacitive, etc.), proximity sensors, force sensors (e.g., strain gauge meter, load cell), vibration sensors, chemical sensors, and/or any other suitable sensors. The sensors can additionally or alternatively include sensors configured to detect and/or determine information associated with identifiers of the system (e.g., identifiers such as described below). However, the system can additionally or alternatively include any other suitable sensors.

The system can optionally include one or more identifiers (e.g., tags). The identifiers can include optical tags (e.g., IR tags and/or beacons, barcodes and/or QR codes, character-based text identifiers, etc.), radio-frequency tags (e.g.; active and/or passive RFID tags; radio beacons, such as those communicating via protocols such as Bluetooth, BLE, Wi-Fi, etc.; etc., which can have limited physical transmission range), magnetic tags (e.g., permanent magnets, electromagnets, etc.), and/or any other suitable tags. The identifiers can be located in and/or on the sensory output device, user, other people, surroundings of the user, remote environments, obstacles and/or regions of interest, and/or any other suitable locations. The identifiers can be arranged in predetermined and/or patterned locations (e.g., regular array, according to a predetermined tag map, etc.), randomly (e.g., wherein the identifiers can subsequently be mapped, such as before and/or during performance of the method), and/or in any other suitable arrangement. The identifiers are preferably configured to be detected and/or analyzed by the sensors and/or communication modules of the system and/or external or auxiliary systems (e.g., RF beacons configured to communicate and/or authenticate with RF communication modules of the system, etc.), but can additionally or alternatively be configured in any other suitable manner. In a specific example, an object proximity to the user (and/or device associated with the user, such as an electronic user device, sensory output device, etc.) and/or user proximity to a receiver (e.g., associated with a known receiver location) can be determined based on the RSSI or other signal strength indicator of a signal transmitted by the identifier. In another example, an object and/or sensory output device orientation relative to the sensory output device and/or receiver, respectively, can be determined based on the signal angle of departure and/or angle of arrival. However, the obstacle or target pose can be otherwise determined.

Figure 6A:
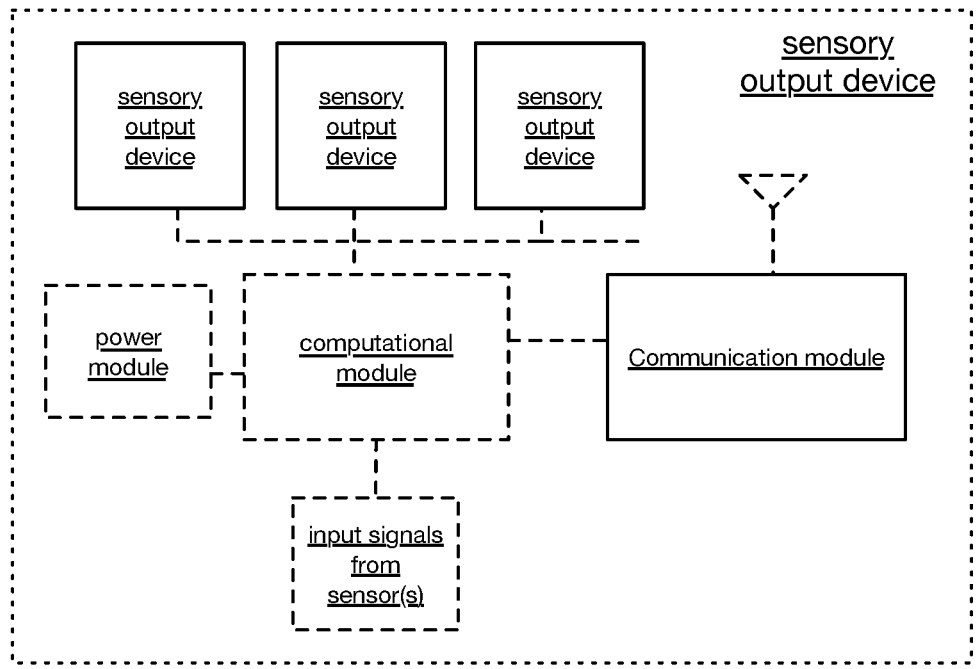
FIGS. 6A-6B depict a schematic of an embodiment of a sensory output device and an example of the embodiment, respectively.
Figure 6B:
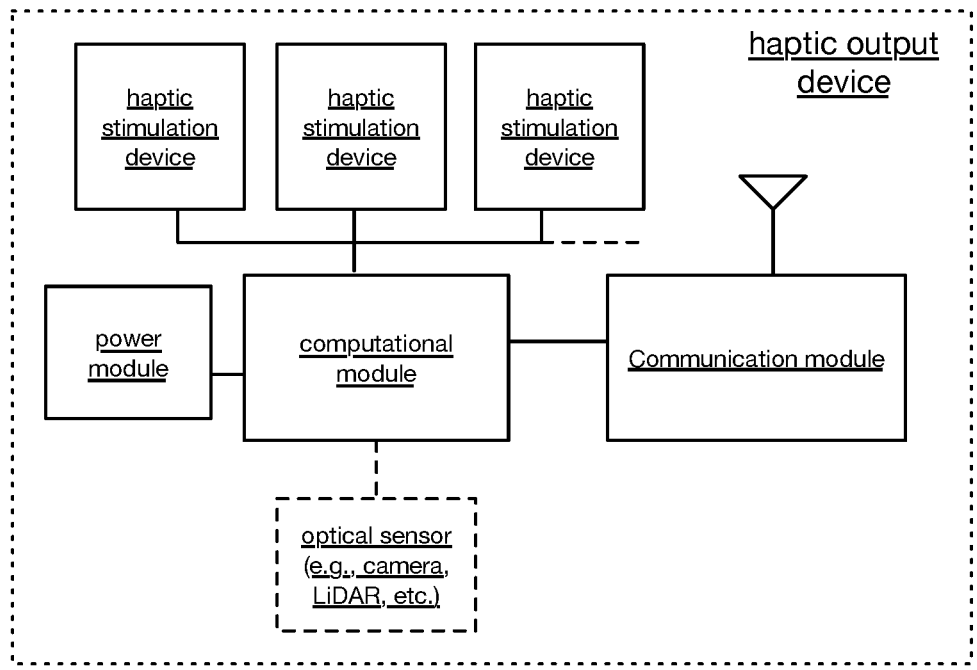

The sensory output device preferably provides stimuli (e.g., through sensory output devices in proximity to the user, such as haptic actuators mechanically coupled to the user), and can optionally include one or more power modules and/or computational modules (e.g., as shown in FIGS. 6A and/or 6B). The device components associated with the stimuli are preferably disposed in a single device, but can additionally or alternatively be disposed across a plurality of devices, and/or be disposed in any other suitable manner.

Figure 2:
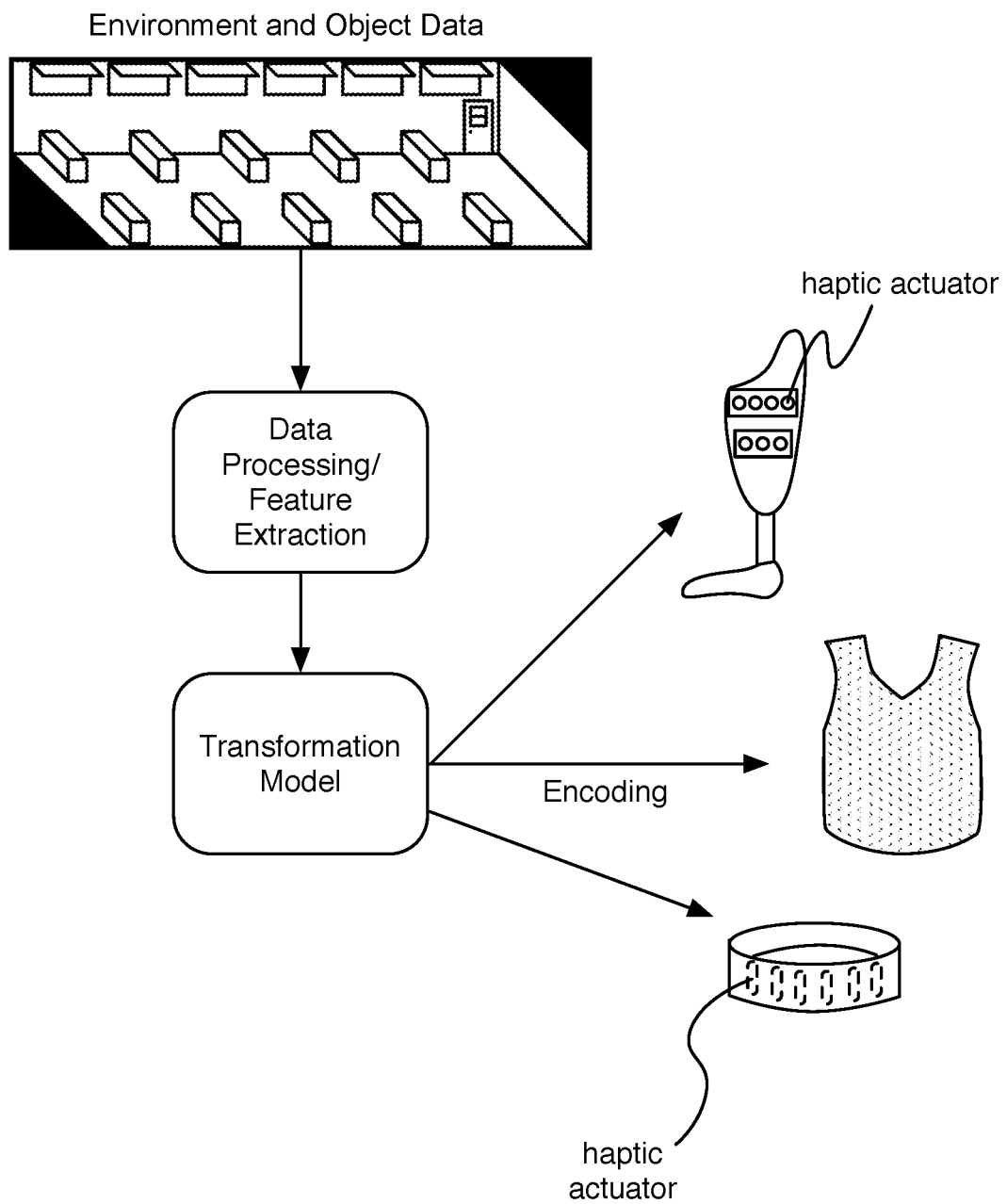
FIG. 2 depicts a schematic of a system and method for providing information to a user.
Figure 3A:
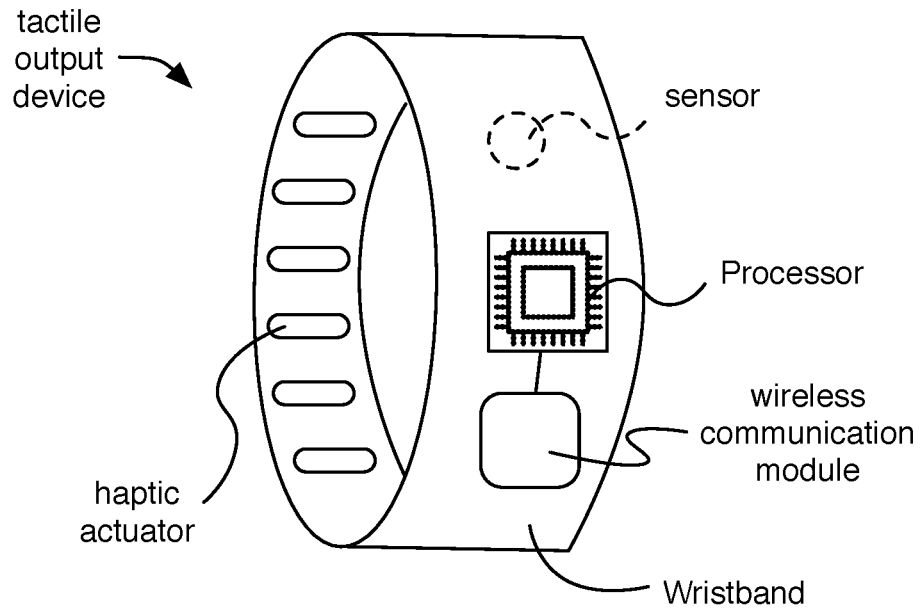
FIGS. 3A-3D depict a first, second, third, and fourth example, respectively, of a device used in a system and/or method for providing information to a user.
Figure 3B:
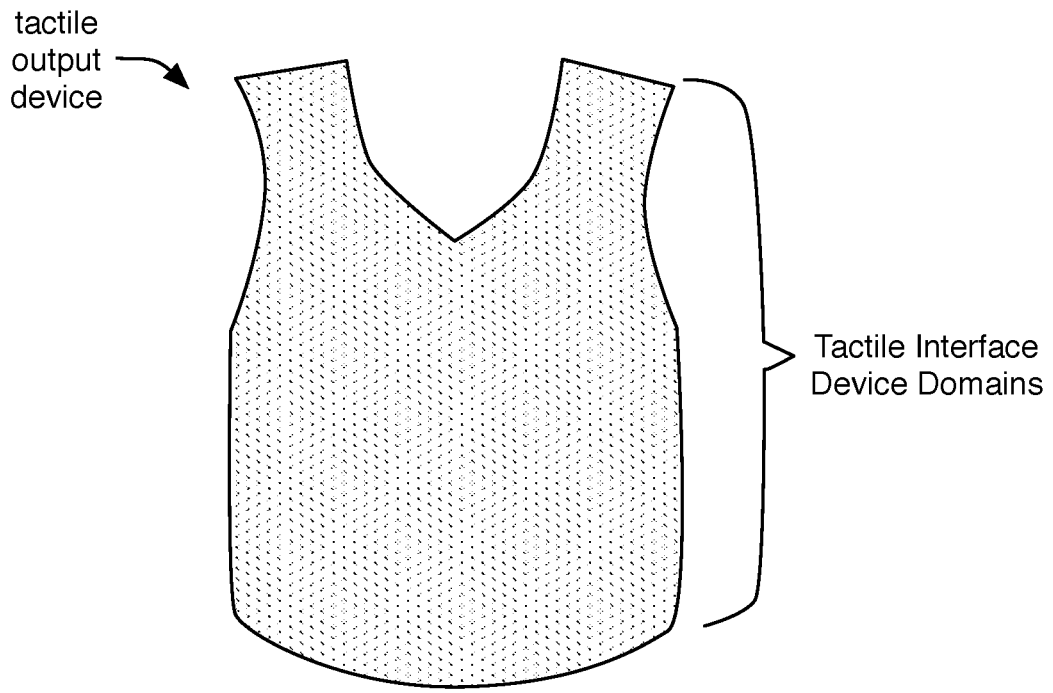
Figure 3C:
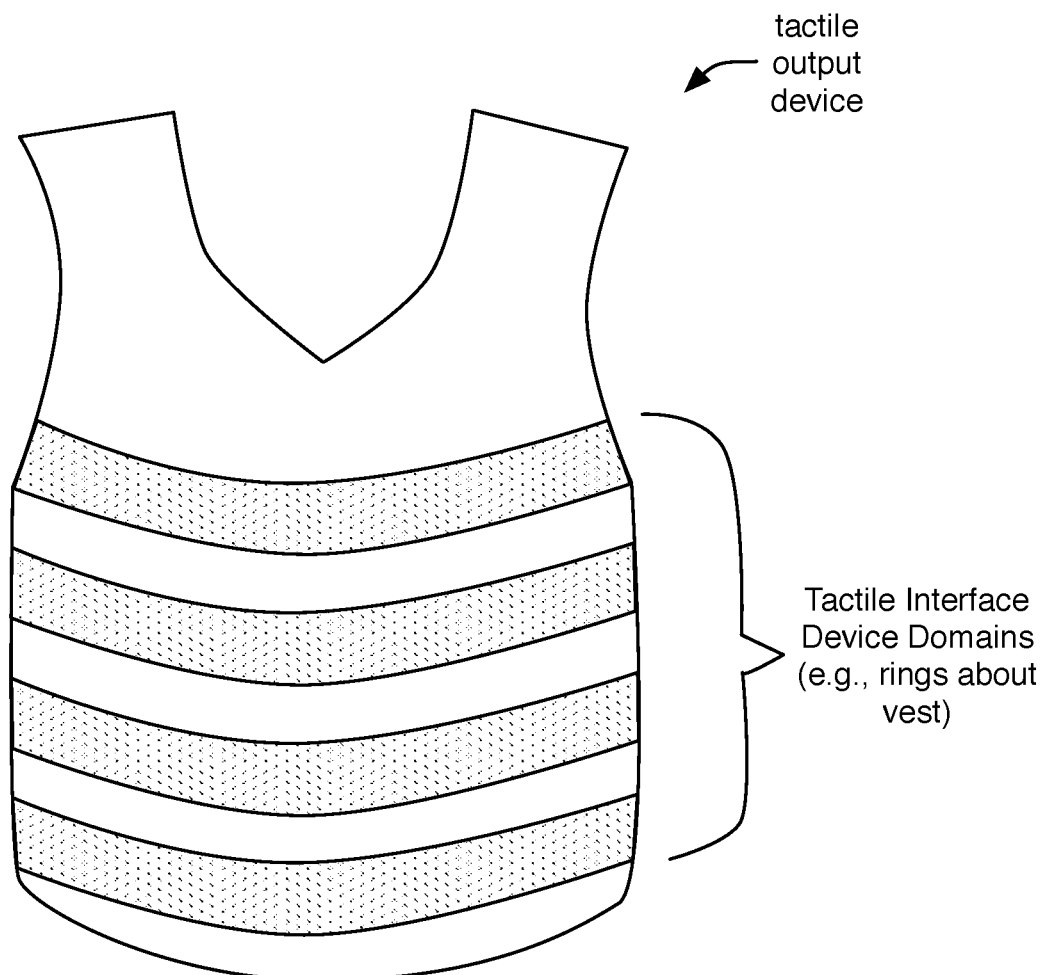

The stimuli can be provided by a plurality of tactile interface devices (e.g., haptic actuators, electrical stimulators, etc.) in a spatial distribution (e.g., multidimensional spatial distribution), each of which can provide a variety of available output stimuli with different stimulus parameters. For example, the device can include one or more arrays of tactile interface devices (e.g., high-density and/or multidimensional array(s), such as shown in FIGS. 2, 3B, and/or 3C; lower-density and/or single-dimensional array(s), such as shown in FIG. 3A; etc.), each of which preferably has a range of available output stimuli with different stimulus parameters. The device(s) can provide haptic stimuli through the tactile interface devices, and in specific examples, can include an array of tactile interface devices operable to provide configurable haptic stimuli to a user. The tactile interface devices can include vibration motors (e.g., eccentric rotating mass (ERM) devices), Linear Resonant Actuators (LRAs), piezoelectric devices, and/or any other suitable devices (and/or combinations thereof, such as hybrid devices incorporating both ERM and LRA elements). However, the tactile interface device(s) can additionally or alternatively include: lights, heating/cooling elements (e.g., Peltier pumps), actuatable tixels (e.g., expandable or retractable regions or protrusions), and/or any suitable tactile interface device.

The device(s) can additionally or alternatively be operable to provide one or more of: auditory stimuli, electrical stimuli (e.g., peripheral stimuli, etc.), olfactory stimuli, taste stimuli, and any other suitable form of stimulus.

The spatial distribution (e.g., array) of tactile interface devices can have a density from 5 devices per $cm^2$ to 50 devices per $cm^2$, or any other suitable density. Furthermore, the spatial distribution of tactile interface devices can be configured with any suitable morphological aspects. The tactile interface devices are preferably arranged in one or more arrays (e.g., high-density arrays). The arrays can include multidimensional arrays (e.g., planar array, 3-dimensional volumetric array, array defined substantially along one or more device surfaces, etc.), single-dimensional arrays (e.g., linear array, curvilinear array, etc.), and/or any other suitable arrays. For example, the device can include a two-dimensional array (e.g., defined substantially on a plane, defined on a curved and/or bent surface, etc.). The arrays can be configured as one or more of: a circular array, an ellipsoidal array, a polygonal array (e.g., a triangular array, rectangular array, a pentagonal array, a hexagonal array, etc.), a circumscribing array, an amorphous array, an array substantially spanning the support structure with which the array is integrated, and any other suitable array type. Additionally or alternatively, the device can include an irregular distribution of tactile interface devices (e.g., arranged substantially on a surface and/or within a volume of the device) and/or any other suitable arrangement of tactile interface devices. Furthermore, the spatial distribution (e.g., array) can be configured across different layers of the overarching device coupled to the user.

The tactile interface device(s) of the array can be controlled as a group, as an array, or be individually indexed and controlled. The tactile interface device(s) can be divided into control domains, wherein each domain (e.g., physical domains of the array of tactile interface devices) can be associated with a different object class, characteristic, or other contextual information type. Different domains can be controlled by the same or individual control systems (e.g., signal drivers, processing systems, etc.). The different domains can be defined as: vertical domains (e.g., vertical strips) and/or horizontal domains (e.g., horizontal bands), be overlapping domains, be the same domain (e.g., wherein different output frequencies, patterns, intensities, or other characteristic can be mapped to different contextual information types), or be otherwise spatially arranged. The different domains can be physically separated (e.g., by a non-zero distance), be contiguous, be overlapping, or be otherwise spatially related.

In a first embodiment, as shown in FIG. 3A, the array of tactile interface devices is integrated with a wrist-region wearable band device, wherein the array is distributed circumferentially about the band surface and coupled to electronics that facilitate provision of haptic stimuli. In this embodiment, the array can be a high-density array, a low-density array (e.g., with a total number of actuators such as 2, 3, 4, 5, 8, 16, 5-10, 10-20, etc.), and/or any other suitable array or other arrangement. In this embodiment, the system preferably includes a housing operable to 1) contain electronics for powering the tactile interface devices and transitioning the tactile interface devices between different modes and/or 2) support the array of tactile interface devices while positioning the array of tactile interface devices in a manner such that the user can sense stimuli provided by the array. The housing can thus be coupled to or otherwise include a fastener that couples the system to a user. The fastener and housing can be of unitary construction or otherwise physically coextensive, or can be otherwise connected, coupled, or couplable. The fastener is preferably operable to be easily and/or repeatably fastened and unfastened manually by the user, and in specific examples, can include a latch, snap, buckle, clasp, hook-and-loop fastening mechanism, and/or any other suitable fastening mechanism, and/or can be operable to expand and contract (e.g., including an elastic element, such as an expansion band; including a deployment clasp, butterfly clasp, or other clasp that is physically coextensive when unclasped; etc.).

In a second embodiment, the tactile interface devices are configured to be carried with a user (e.g., worn by the user, in proximity to the user). In this embodiment, the tactile interface devices are preferably integrated into a wearable garment, wherein the garment can be or include: a top (e.g., shirt, vest, etc.), a bottom (e.g., pants, shorts, skirt, etc.), a headpiece (e.g., headband, earmuffs, hat, etc.), a backpack, an undergarment, socks, and any other suitable form of garment. Additionally or alternatively, the tactile interface devices can be configured to be mechanically coupled to the wearable garment (e.g., retained in one or more pockets of the garment, attached by fasteners such as buttons, clips, magnets, and/or hook-and-loop fasteners, attached by adhesive, etc.). Additionally or alternatively, the tactile interface devices can be configured to attach directly to a user (e.g., by suction, adhesive, etc.), preferably to one or more skin surfaces of the user. Additionally or alternatively, the tactile interface devices can be incorporated into one or more wearable devices (e.g., a head-mounted wearable device, etc.) and/or implanted devices. Additionally or alternatively, the tactile interface devices can be incorporated into prosthetic devices (e.g., lower limb prosthetics, upper limb prosthetics, facial prosthetics, etc.). In an example, such as shown in FIGS. 3B and/or 3C, the array of tactile interface devices can be integrated with a vest garment operable to be worn by a user as the user moves about in his/her daily life.

Figure 3D:
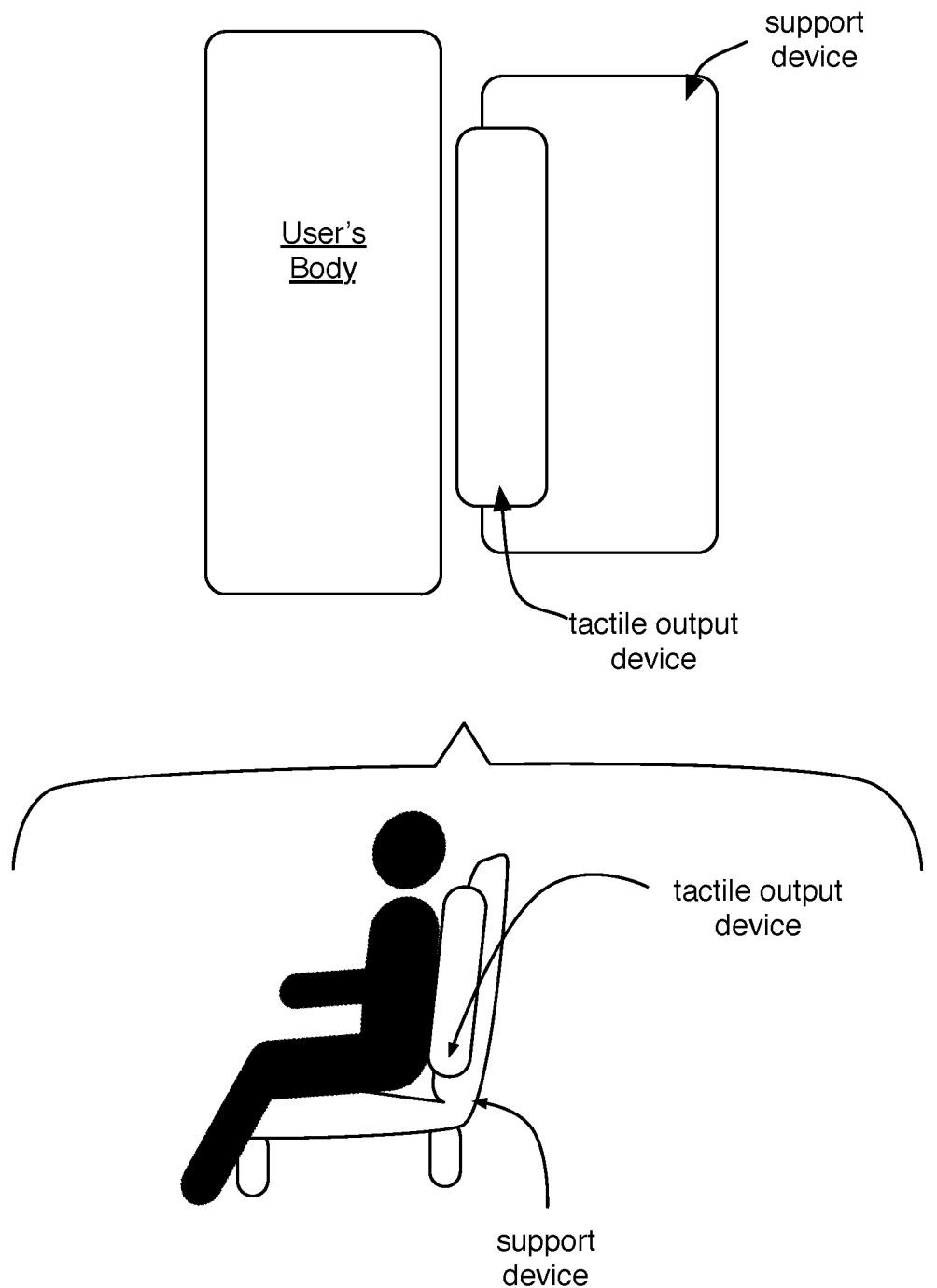

In a third embodiment, the tactile interface devices are configured to be mechanically coupled to the user by a support device that supports the user (e.g., by a support element of the support device), such as shown in FIG. 3D. For example, the tactile interface devices can be integrated into the support element and/or arranged between the user and the support element (e.g., resting on top of the support element). The support devices can include seats (e.g., seats of a vehicle, such as a car or other roadgoing vehicle), couches, beds, platforms (e.g., for sitting and/or standing on), walls, inclined surfaces (e.g., configured to support a leaning user), and/or any other suitable support devices (e.g., as described in U.S. application Ser. No. 15/661,934 titled "Method and System for Determining and Providing Sensory Experiences" and filed on 27 Jul. 2017, which is herein incorporated in its entirety by this reference).

Additionally or alternatively, the tactile interface devices can be disposed in a device configured to be held by the user (e.g., hand-held, held between an arm and torso of the user, held between the legs of the user, etc.). Additionally or alternatively, the tactile interface devices can be disposed in a device configured to rest on the user (e.g., retained against the user by gravity), such as a blanket. However, the tactile interface devices can additionally or alternatively be coupleable to the user (and/or otherwise configured to interact with the user) in any other suitable manner.

In some embodiments, some or all of the tactile interface devices (and/or any other suitable sensory output devices or other devices associated with the system) can be configured to be attached (e.g., permanently, removably, repeatably, etc.) to one or more attachment substrates, such as described in U.S. application Ser. No. 15/716,195 titled "System and Method for Sensory Output Device Attachment" and filed on 26 Sep. 2017, which is herein incorporated in its entirety by this reference. However, the tactile interface devices can additionally or alternatively be attached and/or otherwise coupled to the system in any other suitable manner.

Each tactile interface device (and/or other output unit) is preferably controlled by independent signals and configured to actuate independently from the other output units. Alternatively, a group of output units (e.g., a cluster or subset of the output units) can be independently controlled, such that the group of output units can operate independently from the other output units. Each controlled subset (e.g., individual output unit or cluster) can include one or more output units of the same or different types. In variations, in addition to or in alternative to controlling subsets of actuators (e.g., overlapping and/or disjoint subsets) to convey information as a function of features (e.g. in a first group for a first phoneme or other language component; in a second group, including only actuators not included in the first group, for a second phoneme or other language component; in a third group, including a subset of actuators of the first and second groups, for a third phoneme or other language component; etc.), subsets can be used to map a numerical input to a multi-actuator output. In an example, the actuators can be controlled to make the impression of "sweeps" (e.g., by turning actuators, such as spatially consecutive actuators, on and off in quick succession), such as upward and/or downward sweeps.

Each controlled subset is preferably individually identified, such that it has a locally unique identifier (e.g., index value), but can alternatively share an identifier with a second controlled subset of the device, or be otherwise identified. Each controlled subset (or the respective identifier) is preferably associated with a known, stored spatial position on the device (controlled subset position). The controlled subset position can include an arcuate position, radial position, position along an axis (e.g., lateral axis, longitudinal axis, etc.), set of coordinates, grid position, position relative to another device component (e.g., sensor, different output unit, etc.), or be any other suitable position. The controlled subset positions can be stored by the device (e.g., on volatile or non-volatile memory), can be encoded (e.g., implicitly, explicitly) via a re-indexing module (e.g., reindexing array), and/or stored (and/or otherwise made available) by any other suitable system. However, indexing and/or storing can additionally or alternatively be implemented in any other suitable manner.

Each controlled subset is preferably wired in parallel relative to other controlled subsets of the device, but can alternatively be wired in series, wired in a combination of in parallel and in series, or be wired in any other suitable manner (or not be wired). The controlled subsets of the device are preferably controlled by the processor, but can additionally or alternatively be controlled by a remote computing system (e.g., server system), external device (e.g., mobile device, appliance, etc.), and/or any other suitable computing system.

The sensory output device(s) preferably receive input information from one or more sensors (e.g., configured to receive and/or generate one or more input signals; sensors such as described above and/or otherwise) and/or communication modules (e.g., configured to receive and/or send information, such as sensor data and/or user selections, from and/or to other devices, such as electronic user devices, remote sensors, remote computing systems, etc.).

The communication modules can include wired communication modules (e.g., configured to communicate by wired data connections, such as Ethernet, USB, power line, etc.) and/or wireless communication modules (e.g., radios). The wireless communication modules preferably support (e.g., enable communication using) one or more wireless communication protocols (e.g., WiFi, Bluetooth, BLE, NFC, RF, IR, Zigbee, Z-wave, etc.). However, the system can additionally or alternatively include any other suitable communication modules.

The power module can include one or more power input elements, power storage elements, and/or any other suitable elements. The power module is preferably an electrical power module with an electrical input (e.g., electrical power connection such as a wired connector or inductive loop) and/or electrical storage element (e.g., battery, supercapacitor, etc.), but can additionally or alternatively include any other suitable power input and/or storage elements. The power module can include a battery that is preferably electrically coupled (e.g., connected by conductive wires) to the powered system components, wherein the computational module preferably controls power provision (e.g., as described below), but power provision and/or battery management can additionally or alternatively be performed by any other suitable components.

The computational module can include one or more processors (e.g., CPU or other microprocessor, control circuit, relay system, etc.), computer memory modules (e.g., RAM), computer storage modules (e.g., hard disk drive, flash memory, etc.), and/or any other suitable elements. The computational module is preferably configured to control and/or receive information from the outputs, inputs, communication modules, power modules, and/or any other suitable elements of the system. The computational module can be distributed across multiple systems (e.g., remote server, personal computing device, wearable computing device, mobile computing device, etc.) and/or in the cloud, or can alternatively be implemented in a single computing system.

The computational module is preferably configured to control the controlled subsets (e.g., output units such as tactile interface devices, groups of output units, etc.) individually. In a first example, the processor is configured to provide control signals to each controlled subset (e.g., to a control element of each controlled subset, such as an actuator control circuit). Additionally or alternatively, in a second example, the processor is configured to selectively provide power from the power module to each controlled subset (e.g., by regulating the current provided to each output unit) or to selectively command each controlled subset to enter a mode or attain a set point parameter value (e.g., by communicating a command to an integrated controller of each output unit). However, the computational module can additionally or alternatively be configured to control the controlled subsets in any other suitable manner, or can be configured to not control the controlled subsets.

As described earlier, the system can include embodiments, variations, and examples of the device(s) described in U.S. application Ser. No. 14/750,626, titled "Providing Information to a User Through Somatosensory Feedback" and filed on 25 Jun. 2015, U.S. application Ser. No. 15/661,934, titled "Method and System for Determining and Providing Sensory Experiences" and filed on 27 Jul. 2017, and/or U.S. application Ser. No. 15/696,997, titled "Method and System for Providing Adjunct Sensory Information to a User" and filed on 6 Sep. 2017; however, the system can additionally or alternatively include any other suitable devices and/or device elements.

3. Method

Block S110 recites: determining environmental information (e.g., receiving a dataset representative of a distribution of a set of objects within an environment of the user), which preferably functions to provide one or more sources of information that can be processed and delivered to the user in a new format, according to subsequent blocks of the method 100.

Block S110 can implement one or more system components (e.g., sensors of the system, such as local sensors, remote sensors, etc.) operable to collect data that is representative of objects in the environment of the user and/or data that is representative of other aspects of the environment of the user. In relation to objects in the environment of the user, Block S110 can thus implement systems operable to use or detect one or more of: radiation (e.g., light in the visible spectrum, light in the ultraviolet spectrum, light in the infrared spectrum, radio waves, other forms of radiation), heat, sound waves, electrical fields, physical interactions (e.g., touch, smell, etc.), any suitable form of energy that can be detected from objects in the environment, and any other suitable form of energy that can interact with objects in the environment to produce an observable signal. As such, systems and data types can be selected based upon sensor type, accuracy, resolution, range, susceptibility to environmental conditions, and any other suitable factors related to object detection. In variations, Block S110 can thus include receiving one or more of: light detection and ranging (LIDAR) data, radar signals, image data (e.g., which can be processed using photogrammetric techniques), sonar/echolocation data, infrared data, audio data, and any other suitable types of data.

In Block S110, some or all information determined (e.g., data collected) preferably includes or can otherwise be processed to generate three-dimensional (3D) representations of objects in the environment of the user. As such, in variations Block S110 can include receiving or generating one or more of: point cloud data, surface mesh data, or other 3D model data. Block S110 can additionally or alternatively include determining two-dimensional (2D) and/or other representations of objects in the environment of the user (e.g., receiving and/or otherwise determining planar map information, such as street maps, pedestrian path maps, building maps, room maps, etc.).

Furthermore, Block S110 can include directly collecting the data at variations of systems described above, wherein the systems include transmission devices (e.g., lasers, radio transmission devices, sound wave transmission devices, etc.), sensors (e.g., optical detection sensors, radar sensors, microphones, infrared sensors, etc.), and storage devices. However, Block S110 can omit data collection, and instead include receiving collected data directly from storage devices.

In a first specific example, Block S110 can include receiving 3D point cloud data of an environment of the user, wherein the 3D point cloud data is acquired using a LIDAR system. In a second specific example, Block S110 can include using an infrared light projector to project light through infrared sources, wherein the projected light interacts with objects in the environment and is detected with one or more infrared cameras. In a third specific example, Block S110 can include receiving and processing radar data associated with environmental objects, based upon interference, reflection, transmission, and/or other radar characteristics. In a fourth specific example, Block S110 can include projecting sound waves with known characteristics into the environment, and receiving reflected and/or transmitted sound waves that have interacted with environmental objects. However, Block S110 can additionally or alternatively include receiving any other suitable type of data that is representative of the environment (e.g., objects in the environment) of the user (and/or any other suitable real and/or virtual environments).

For instance, Block S110 can include receiving data associated with environmental features that are not necessarily objects, but that can interact with the user and/or affect the user physically. In examples, Block S110 can include receiving data associated with heat sources or other areas of high temperature (e.g., a region near a hot stove or oven using infrared sensors, temperature sensors, device states, etc.), regions near electrical hazards, regions of high moisture content, regions of poor air quality, and/or any other suitable non-object environmental features.

Block S110 can additionally or alternatively include determining information associated with the user, such as people of interest (e.g., determined based on social graph information, such as that determined or queried from a social networking system; company directories; stored contacts; manual inputs; etc.), destinations (e.g., determined based on manual inputs, calendar entries, historical travel, current user trajectory, etc.), and/or any other suitable information.

In some variations, Block S110 includes determining position and/or orientation information at one or more sensors. For example, Block S110 can include determining the position and/or orientation of the user (and/or a sensory output device coupled to the user, such as a garment or band worn by the user), such as based on sensors (e.g., GPS receiver; RF communication systems, such as Wi-Fi radios; IMU sensors, such as magnetometers, gyroscopes, and/or accelerometers; sensors configured to detect identifiers in the environment; etc.) attached to the sensory output device and/or otherwise associated with the user (e.g., integrated with an electronic user device, such as the user's smartphone). User position and/or orientation can be determined relative to a global coordinate system (e.g., based on GPS systems, RF-based geopositioning techniques such as Wi-Fi SSID-based geopositioning services, magnetometer data, etc.), relative to local reference points (e.g., based on detection of the local reference point at sensors coupled to the user, based on detection of the user (and/or associated identifiers or devices) at sensors coupled to the local reference point, based on detection of both the user and the local reference point at external sensors, etc.; using sensors such as cameras, lidar systems, RF sensors, other sensors such as those described above regarding the system, etc.), dead reckoning (e.g., based on IMU or other motion sensor information), and/or relative to any other suitable references. Block S110 can additionally or alternatively include determining user motion (e.g., based on measurements from sensors such as IMU sensors; based on changes in user position, such as position determined as described above; etc.) and/or any other suitable spatial information associated with the user.

Block S110 can additionally or alternatively include determining the motion, position, and/or orientation of other people (e.g., persons of interest to the user, people associated and/or not associated with the user, etc.) and/or objects. Such motion, position, and/or orientation information can be determined in an analogous manner as described above regarding the user motion, position, and orientation, and/or can be determined in any other suitable manner. In a first specific example, such information is determined based on sensors (e.g., GPS receiver, IMU sensors, etc.) carried by and/or otherwise associated with the people (e.g., other electronic user devices, such as other people's smartphones). In a second specific example, such information is determined based on other sensors (e.g., fixed sensors within the environment, such as cameras and/or LiDAR systems; sensors associated with the user, such as sensors integrated with the sensory output device and/or electronic user device; etc.). However, Block S110 can additionally or alternatively include determining any other suitable information in any suitable manner.

Block S120 recites: determining a set of features based on the information (e.g., extracting a set of features characterizing the set of objects, the set of features including a first feature set associated with characteristics of the set of objects, a second feature set associated with interactivity between the user and the set of objects, and a third feature set associated with the environment of the user). Block S120 preferably functions to extract key features from the information determined in Block S110 (e.g., wherein the key features pertain to objects or other features present in the environment of the user, with which the user may interact).

A first feature set can be associated with characteristics inherent to each of the set of objects and/or classifications of the set of objects according to one or more definitions. In relation to object characteristics, in variations, the first feature set can be associated with one or more of the following for each of the set of objects: morphological features (e.g., shape, size), surface features (e.g., texture, sharp features, etc.), aesthetic features (e.g., color), motility, movement patterns, modularity, mechanical features (e.g., stiffness, elasticity, etc.), physical features (e.g., mass, density, temperature, electrical charge, etc.), and any other suitable characteristic physical features.

In relation to classifications of the set of objects, in variations, the first feature set can be associated with classifications at one or more levels or hierarchies. For instance a highest hierarchy can be associated with one or more of the following classifications for each of the set of objects: animate vs. inanimate, living vs. non-living, and any other suitable higher level classification. Then, each of the set of objects can be classified at a next classification level. For instance, in relation to animate objects, lower level classifications can be associated with humans (e.g., known humans and/or persons of interest, strangers) vs. non-humans or other taxonomic levels. Similarly, in relation to inanimate objects, lower level classifications can be associated with inanimate object types (e.g., furniture, appliances, vehicles, etc.). However, any other suitable classification regime in the first feature set can be used.

Extraction of the first feature set from the data received in Block S110 can be implemented using one or more classification algorithms including one or more of: lumping and splitting algorithms, artificial neural networks, category learning algorithms, clustering, pattern recognition techniques, and any other suitable classification algorithms. Furthermore, classification algorithms can be trained using machine learning techniques, and in variations, the machine learning technique(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naive Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning technique.

A second feature set can be associated with interactivity between the user and environmental features such as objects of the set (e.g., thereby including aspects associated with the user's ability to interact with the each of the set of objects in a beneficial manner and/or for the set of objects to interact with the user in an undesired manner). In variations, the second feature set can be associated with one or more of the following for each of the set of objects: distance between the object and the user; direction vectors between the user and objects of interest (e.g., position of the object relative to the user, preferably accounting for both user position and user orientation, but alternatively based on user position and a fixed reference orientation and/or based on any other suitable coordinates); relative heights between the objects and the user; relative motion (e.g., velocity, acceleration, etc.) between the object and the user; features associated with the types of interactions available between the user and the object; features associated with a risk profile of the object (e.g., features indicative of a maximum amount of damage that could result from an interaction between the object and the user, features indicative of a minimum amount of damage that could result from an interaction between the object and the user, etc.); features associated with a benefit profile of the object (e.g., features indicative of a benefit that could be gained as a result of an interaction between the object and the user); and any other suitable interactivity features. In one example, potentially useful objects can include points of interest (e.g., restrooms, water fountains, vendors and/or vending machines, etc.). However, the potentially useful objects can additionally or alternatively include any other suitable objects.

The second feature set can additionally or alternatively include characteristics associated with the environment itself (e.g., rather than and/or in addition to the objects within it). For example, such characteristics can include environmental classifications, such as purposes and/or functionalities associated with the environment. In a first example, such classifications include classifications associated with regions of an organization's building and/or campus (e.g., determined based on an organization map, such as from internal map data), such as departments and/or building types (e.g., warehouse, manufacturing, research & development, legal, etc.; physics, biology, comparative literature, electrical engineering, etc.;). In a second example, such classifications include classifications associated with regions of an urban area (e.g., determined based on a map such as a municipal or regional map), such as municipal zones and/or districts (e.g., theater district, financial district, residential zone, commercial zone, light industrial zone, etc.). However, the second feature set can additionally or alternatively include any other suitable characteristics.

Extraction of the second feature set can be derived from analyses of states of the user and each of the set of objects. As such, in examples, generating portions of the second feature set can include processing of position, velocity, acceleration vectors, and or derivative metrics between the user and each of the set of objects. Extraction of the second feature set can additionally or alternatively be derived from the characterizations of the first feature set, in relation to benefit, harm, and/or potential interactions that could occur between the user and each of the set of objects. The second feature set can be generated or trained using machine learning techniques, as described in relation to the first feature set above.

In a first variation, determining a position of an object relative to the user (e.g., for inclusion in the second feature set and/or any other suitable feature set) includes: determining a position and/or orientation of the user relative to an external reference (e.g., a fixed coordinate system, a global or local map, a fixed object within the environment, etc.); determining a position (and/or orientation) of the object relative to the external reference (and/or to another external reference, such as wherein a spatial relationship between the two external references is known or can be determined); and, based on the positions and/or orientations of the user and the object, determining the position of the object relative to the user. In a second variation, determining a position of an object relative to the user includes sampling sensor measurements directly indicative of the relative position. In examples, such sensor measurements can include: at a sensor associated with (e.g., carried by, mechanically coupled to, etc.) the user, sampling measurements indicative of the relative position of the object (e.g., data, such as camera images, lidar data, etc., that includes a representation of the object); at a sensor associated with the object, sampling measurements indicative of the relative position of the user; and/or at an external sensor (e.g., not mechanically coupled to the user or the object), sampling measurements indicative of the spatial relationship between the object and the user. However, the second feature set can additionally or alternatively be determined in any other suitable manner.

A third feature set can be associated with the environment of the user (e.g., thereby characterizing aspects of the environment that could either affect the user and/or the set of objects, and/or could promote or obstruct interactions between the user and the set of objects). In variations, the third feature set can describe one or more of the following: environment-attributed paths or trajectories between the user and each of the set of objects; boundaries attributed to the environment (e.g., walls, ceilings, floors, etc.), environmental terrain features (e.g., upsloping terrain, downsloping terrain, uneven terrain, loose terrain, homogenous terrain, slippery terrain, stairs, such as stairs extending upward and/or downward from a user position or current elevation, etc.), environmental conditions (e.g., temperature, humidity, pressure, lighting conditions, sound-related features, air quality, etc., and any other suitable features associated with the environment of the user.

Extraction of the third set of features can be performed using environmental sensors (e.g., temperature sensors, optical sensors, humidity sensors, microphones, light sensors, pressure sensors, etc.) configured throughout the environment of the user. Extraction of the third set of features can additionally or alternatively include processing of the data received in Block S110 to extract environmental features. Extraction of the third set of features can additionally or alternatively include processing of data associated with known and/or indicated objects in the environment (e.g., predetermined map data). However, the third set of features can additionally of alternatively be extracted in any other suitable manner.

Block S120 can additionally or alternatively include determining features associated with user navigation (e.g., waypoint-based navigation, turn-by-turn navigation, etc.). For example, Block S120 can include determining a route for user traversal (e.g., pedestrian traversal) to a destination (e.g., destination determined in Block S110, such as a destination received from the user), preferably from the user's current position. The route can be defined by traversal paths, waypoints (e.g., vertices of the paths), and/or any other suitable route elements. For example, route determination can include, based on the destination (e.g., determined in Block S110) and preferably on the current user location, determining a series of waypoints for user traversal to the destination (e.g., using map data and/or sensor measurements to determine the paths and/or waypoints). The waypoints can optionally be handled similarly to environmental objects, wherein characteristics of one or more waypoints (e.g., the next waypoint in the series, the next several waypoints, all waypoints, etc.), such as position relative to the user (e.g., distance, heading, etc.), can be determined and/or included in the set of features.

Route determination can optionally include determining multiple routes to a destination (e.g., alternate routes, such as to allow for route blockages and/or user preferences), routes to multiple destinations (e.g., wherein a user plans to travel to multiple destinations, such as in an arbitrary order; multiple candidate destination, such as wherein the user's final destination is not yet known; etc.), and/or any other suitable number of routes of any suitable type. The multiple routes can optionally share waypoints (e.g., wherein waypoints for overlapping route portions are determined once and shared by all relevant routes).

In relation to Block S120, the method 100 can include performing any suitable filtering operations with the feature sets. For instance, the feature sets can be filtered to remove features not of interest to the user (e.g., based upon sensory impairment details, based on personal interest, based on professional interests, etc.). Additionally or alternatively, In relation to Block S120, the method 100 can include performing any suitable prioritization operations with the feature sets. For instance, the feature sets can be processed with a ranking algorithm that prioritizes features of interest to the user (e.g., based on sensory impairment details, based on personal interest, based on professional interests, etc.) or de-prioritizes features not of interest to the user. However, Block S120 can include post-processing or pre-processing the features sets in any other suitable manner.

Furthermore, Block S120 can include extracting any other suitable feature sets and/or organizing the feature sets in any other suitable manner.

Block S130 recites: determining output parameters based on the features (e.g., implementing a transformation model with the set of features, the transformation model operable to transform the set of features into a set of output parameters in a device domain, the device domain associated with a distribution of tactile interface devices coupled to the user and output aspects of the distribution of tactile interface devices). Block S130 preferably functions to use features of interest extracted in Block S120, to generate multi-domain encodings associated with outputs of a device coupleable to the user (e.g., sensory output device, such as described above regarding the system). As such, Block S130 functions to facilitate transformation of object features, object-user interaction features, and environment-derived features into signals that can be output using a device coupled to the user (e.g., by encoding feature-derived components for use in controlling outputs of the device).

The transformation model can optionally generate output components associated with control signals that activate devices of the set of tactile interface devices (e.g., wherein the control signals can be executed in Block S150 of the method 100). In variations, the transformation model can include performing one or more of the following: a linear Predictive Filtering/Coding (LPC) operation, that produces a set of filter coefficients and an energy parameter, wherein the filter coefficients can be converted to frequency-locations in a line spectral pair (LSP) representation (e.g., line spectral frequencies), and the energy parameter is mapped to a stimulus parameter (e.g., intensity, amplitude, duration, etc.); a decomposition transformation operation, where each dimension represents how much of a basis function is present; a single global axis mapping operation, wherein the possible range of frequencies may be discretized to a set of frequency bands based on the number of tactile interface devices in the array and each element represents represent a band of frequencies; a multiple local axis mapping operation, wherein each LSP is given a different set of tactile interface devices to represent a range of frequencies; a coded local axis mapping operation, wherein each LSP is given a different set of axis representative of the frequency domain using a tree-type code (e.g., a binary code with different levels for different frequency ranges or functions); and any other suitable encoding or mapping operation.

The transformation model can be implemented using a computational module that retrieves a physical layout for the set of tactile interface devices (e.g., from storage, from inputs provided by a user or operator, etc.). Encoding and mapping can additionally or alternatively be implemented in any other suitable manner, such as described in U.S. application Ser. No. 14/750,626, titled "Providing Information to a User Through Somatosensory Feedback" and filed on 25 Jun. 2015.

In relation to the feature sets described in Block S120 above, the transformation model(s) of Block S130 can transform, encode, or otherwise map feature sets associated with the set of objects to one or more of: subdomains (e.g., subregions, sub-clusters, sublayers, etc.) of the array of tactile interface devices; different stimulus aspects associated with the array of tactile interface devices; and any other suitable aspects of the array of tactile stimulus devices.

Figure 4A:
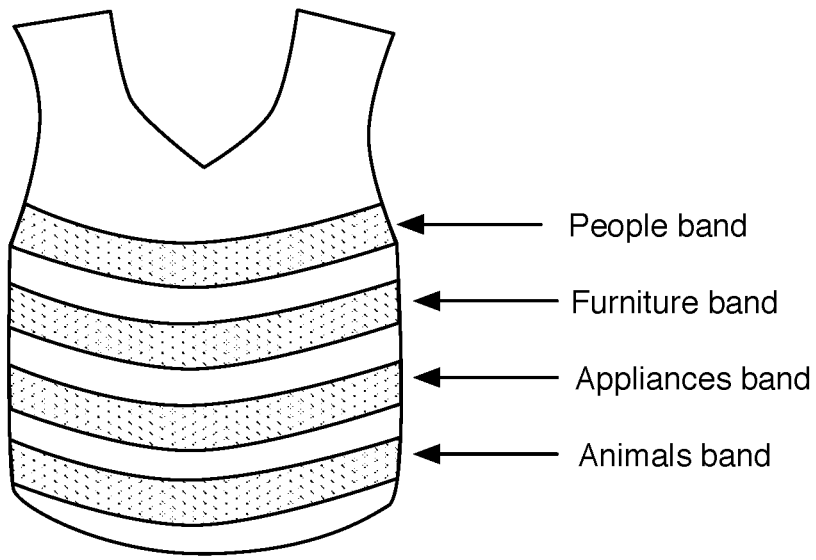
FIGS. 4A-4D depict specific example outputs of an embodiment of the method.
Figure 7A:
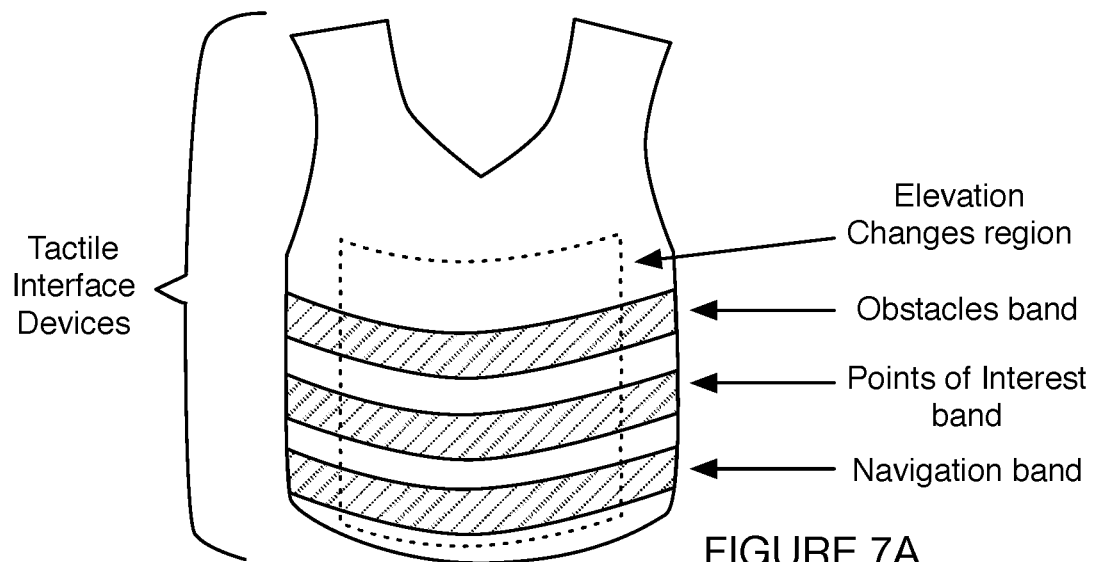
FIGS. 7A-7D depict specific example outputs of an embodiment of the method.

In variations related to feature sets described in Block S120 above, the transformation model can transform, encode, or otherwise associate aspects of the first feature set with domains (e.g., layers, regions, clusters, areas, etc.) of the array of tactile interface devices, examples of which are shown in FIGS. 4A and 7A. As such, inherent characteristics and/or classifications of the set of objects in the environment of the user can be mapped to different domains of the array of tactile interface devices. For instance (e.g., in a device variation that has a distribution of the array of tactile stimulation devices configured in a set of rings (or physical bands) about the torso of the user, such as with the array coupled to an upper garment; configured in a set of rings about another body part of the user; etc.), such a mapping can include: a first ring of the array of tactile stimulation devices can be associated with objects that are characterized as inanimate objects, and a second ring can be associated with objects that are characterized as animate objects. In this example, the first region can surround a superior portion of the body of the user (e.g., the chest of the user) and the second ring can surround an inferior portion of the body of the user (e.g., the waist of the user). Additionally or alternatively, such a mapping can include: a first ring associated with navigation information (e.g., providing stimuli associated with one or more upcoming waypoints), a second ring associated with points of interest (e.g., people, objects, and/or location that may be of interest and/or utility to the user), and a third ring associated with obstacles (e.g., that the user may need to navigate past). However, variations of the example can additionally or alternatively associate rings of the set of tactile stimulation devices with object characteristics or classifications in any other suitable manner. Additionally or alternatively, in a device variation that has a distribution of the array of tactile stimulation devices, a first subregion of the array can be associated with a first classification of predominant object types in the environment (e.g., furniture in the room), a second subregion of the array can be associated with a second classification of predominant object types (e.g., people the user knows), and a third subregion of the array can be associated with a third classification of predominant object types. In variations of the example, the subregions can have any suitable shape and occupy any suitable region of a support structure coupled to the user's body.

In the examples and variations described above, the domains/regions of the array of tactile stimulation devices can be fixed or dynamically modifiable. For instance, the subdomain can be dynamically modified, according to the encodings performed in Block S130, in order to match a shape of an object (e.g., a dog can be represented with a dog-shaped region of the array of devices). In another example, characteristics of the objects can further represented with dynamically modifiable subdomains. For instance, a larger object can be mapped to a larger subdomain, and a smaller object can be mapped to a smaller subdomain. However, characteristics of the set of objects can be represented in any other suitable manner.

Figure 7B:
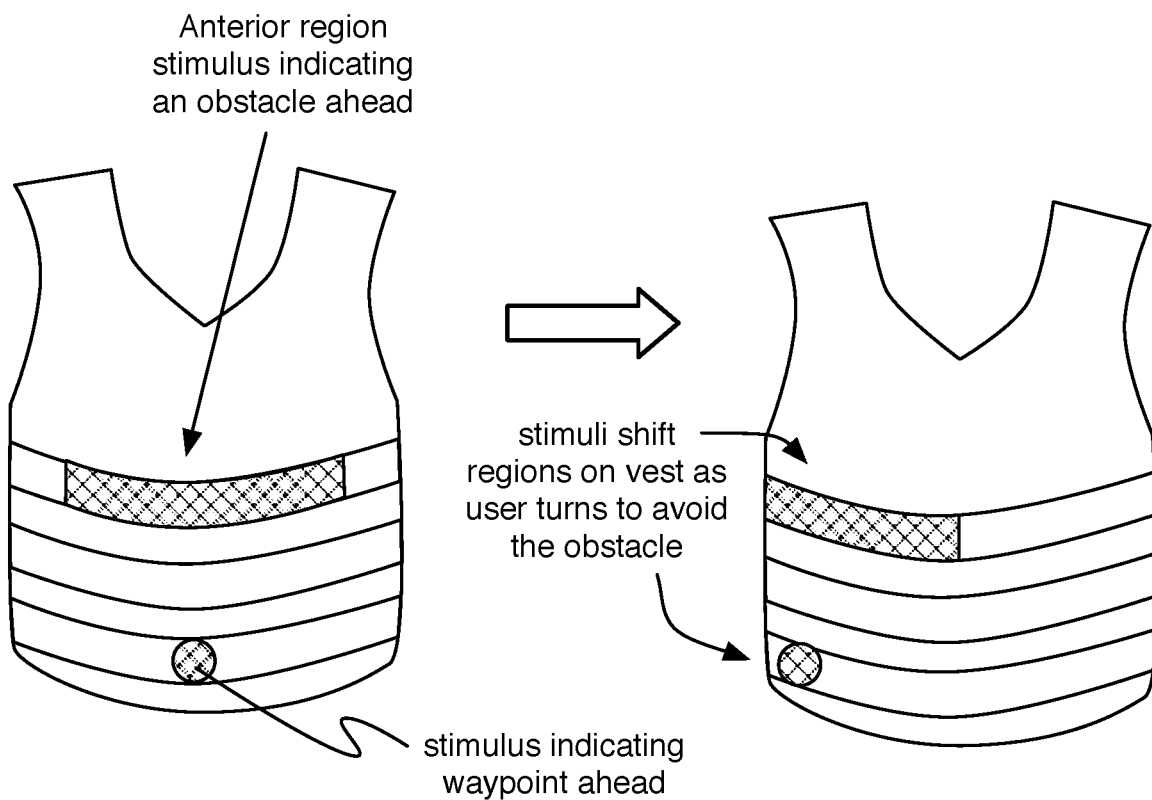

In a first embodiment, the transformation model produces encodings that result in subdomains of an array of tactile stimulation devices that are closest to an object (e.g., nearby object in the environment, remote object, navigation waypoint, etc.) outputting a stimulus associated with that object (e.g., anterior devices for an object in front of the user). For example, the method can include: determining a position of an object relative to the user; selecting a band to associate with the object (e.g., based on an object classification, such as navigation-related, obstacle, point of interest, etc.); selecting a region of the selected band based on the object's relative position (e.g., in response to determining that the object is at a 27° heading relative to the user, selecting a region centered on a 27° angular position within the band); and providing stimulus to the user at the selected region, wherein the stimulus is indicative of the object (e.g., stimulus characteristics, such as intensity, spatial and/or temporal pattern, "texture", etc., determined based on characteristics of the object). In this example, in response to movement of the user and/or object, the stimulus region is preferably updated accordingly (e.g., as shown in FIG. 7B). This embodiment is preferably used in association with a sensory output device that couples to (e.g., encircles, adheres to, etc.) a portion of the user's body for which the portion's orientation tends to be relatively similar to the user's current and/or anticipated direction of motion (e.g., torso, head, leg, etc.), but can additionally or alternatively be used with sensory output devices coupled to any other suitable portion of the user (e.g., one or more portions of the arm, such as the wrist or forearm, etc.).

In a second embodiment, the transformation model produces encodings wherein the orientation of an object relative to the user (e.g., relative to a first portion of user, such as the user's head, torso, etc.) is mapped onto an orientation of the sensory output device (e.g., relative to an internal reference, like a front portion of the device; relative to a second portion of the user, preferably the portion to which the device is coupled, such as the user's wrist, forearm, ankle, etc.). In one example, the sensory output device includes a bracelet-style housing configured to encircle the user's wrist. In this example, a dorsal portion of the bracelet (e.g., bracelet portion configured to contact a dorsal portion of the wrist, bracelet portion currently contacting a dorsal portion of the wrist, etc.) is mapped to an anterior of the user, a volar portion of the bracelet is mapped to a posterior of the user, an ulnar portion of the bracelet is mapped to a proximal side of the user (e.g., for a right wrist, the right side), and a radial portion of the bracelet is mapped to a distal side of the user (e.g., for a right wrist, the left side), preferably such that, when the user's arm lies along the length of their body with the palm facing toward the posterior, the two mappings are substantially aligned. In this embodiment, the transformation model preferably produces encodings that result in subdomains of an array of tactile stimulation devices that map to an object's orientation relative to the user outputting a stimulus associated with that object (e.g., a dorsal subregion of devices for an object in front of the user). The transformation model is preferably implemented as described above regarding the first embodiment, while accounting for this mapping between the user—object orientation and the sensory output device orientation, but can additionally or alternatively be implemented in any other suitable manner. This embodiment is preferably used in association with a sensory output device that couples to (e.g., encircles, adheres to, etc.) a portion of the user's body for which the portion's orientation tends to change significantly relative to the user's current and/or anticipated direction of motion (e.g., one or more portions of the arm, such as the wrist or forearm, etc.), but can additionally or alternatively be used with sensory output devices coupled to any other suitable portion of the user (e.g., torso, head, leg, etc.).

In some variations (e.g., wherein the sensory output device includes a low density and/or total number of output actuators, such as a wristband with 4 or 8 haptic actuators arrayed about the circumference of the band), the method can include adjusting the actuation intensity of some of the actuators (e.g., neighboring actuators), such as to cause the user to perceive the actuation as being centered at a (tunable) position between the controlled actuators (e.g., at a position without an actuator). For example, in a device that includes 4 haptic actuators in a circumferential band, located at (or corresponding to a user orientation of, such as described above regarding the second embodiment) 0°, 90°, 180°, and 270°, an object at a 45° heading can be represented by equal-intensity actuation of the 0° and 90° actuators. In this example, as the object's heading changes, the relative intensities of the actuators can be adjusted accordingly (e.g., when the object is at a 60° heading, the 90° actuator actuates at a greater intensity than the 0° actuator, such as at twice the intensity; when the object is at a 90° heading, only the 90° actuator actuates; when the object is at a 135° heading, the 90° and 180° actuators actuate at equal intensities; etc.).

However, the transformation model can additionally or alternatively produce any other suitable encodings in any suitable manner.

Figure 7C:
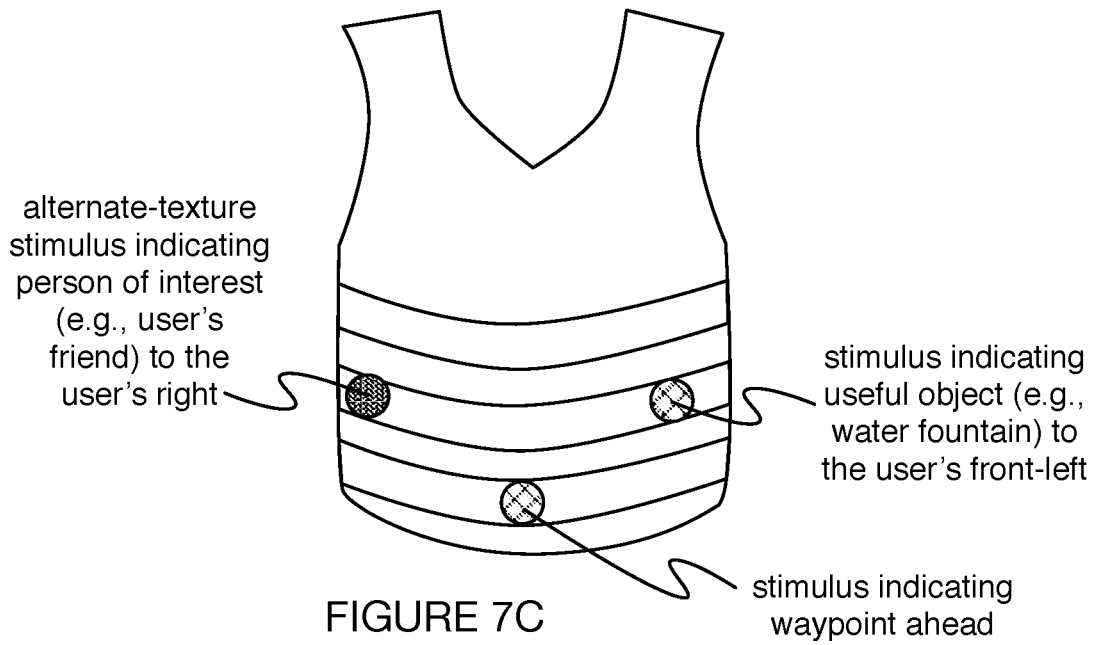

In variations related to feature sets described in Block S120 above, the transformation model can additionally or alternatively transform, encode, or otherwise associate aspects of the second feature set with stimulus parameters of the array of tactile interface devices. In variations, the transformation operation can result in subdomains of actuators providing stimuli according to a range of parameter types, based upon interactivity between the user and one or more objects (e.g., wherein interactivity features are derived from the second feature set). In variations, stimulus parameters can include one or more of: temporal output type (e.g., intermittent, pulsed, continuous, etc.); pulse pattern (e.g., different periodic and/or aperiodic patterns); pulse waveform characteristics (e.g., sinusoidal, square wave, triangular wave, wavelength, etc.; such characteristic may affect a user's perception of the "texture" of the stimulus), output amplitude, output intensity; output duration; out pulse duration, etc.), device domains involved in an output (e.g., stimulus position, size, spatial sharpness or diffuseness, spatial pattern, etc.), and any other suitable stimulus parameter (e.g., as shown in FIG. 7C).

Figure 4B:
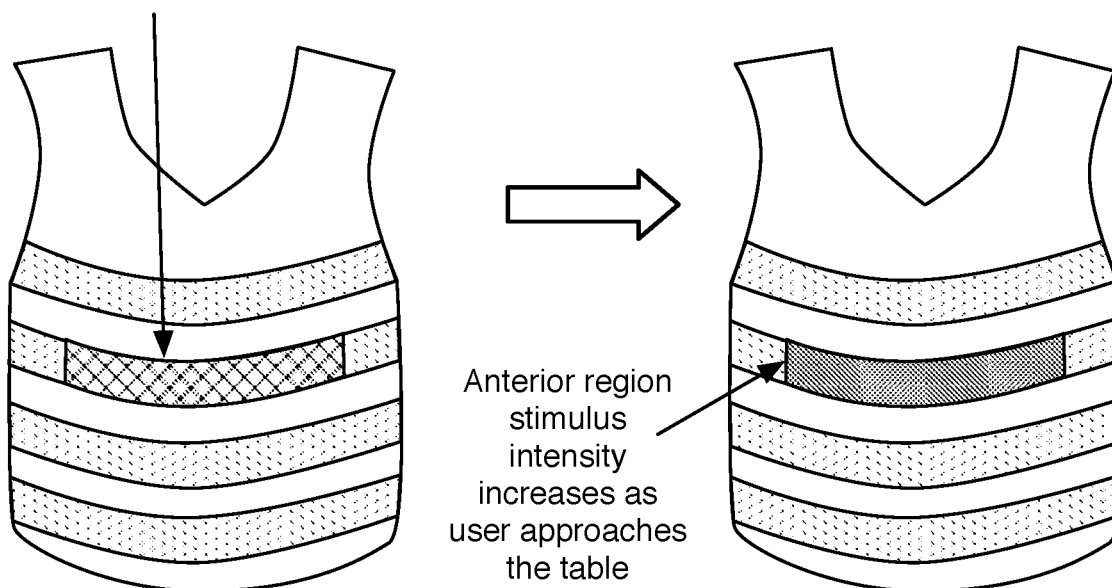

For instance, in a device variation that has a distribution of the array of tactile stimulation devices configured in a set of rings (or bands) about the torso of the user (e.g., with the array coupled to an upper garment): the transformation model can produce encodings that produces vibration in devices of a ring, associated with objects (and/or waypoints), wherein the intensity of vibration increases as the user approaches an object, as shown in FIG. 4B. Additionally or alternatively, temporal patterns and/or textures can be altered based on the distance. For example, far-off objects can be represented by constant, low-intensity actuation, whereas close objects can be represented by pulsing actuation (e.g., wherein a period of the pulsing decreases as the object gets closer). In navigation-related examples, upcoming waypoints can optionally be presented to the user depending on proximity to the current waypoint. For example, as a user approaches a waypoint ahead of them, the waypoint-associated stimulus at the anterior region of the device can increase in intensity and begin pulsing; as the user gets closer yet (e.g., within 5 m, 2 m, 1 m, 0.5 m, 0.1-1 m, 1-10 m, etc.), a second waypoint stimulus (e.g., lower-intensity stimulus) can be provided corresponding to the following waypoint (e.g., if the user should turn left at the upcoming waypoint, the second stimulus can be provided on the left side of the device).

Additionally or alternatively, the transformation model can produce encodings that result in outputs that sweep across a subdomain of the array of tactile interface devices, wherein the sweeping behavior corresponds to velocity and direction of an object moving in front of the user. Additionally or alternatively, the transformation model can produce a high intensity pulse for an object that could potentially harm the user (e.g., a sharp or hot object). However, variations of the examples can produce any other suitable encoding between features and stimulus parameters.

Figure 4C:
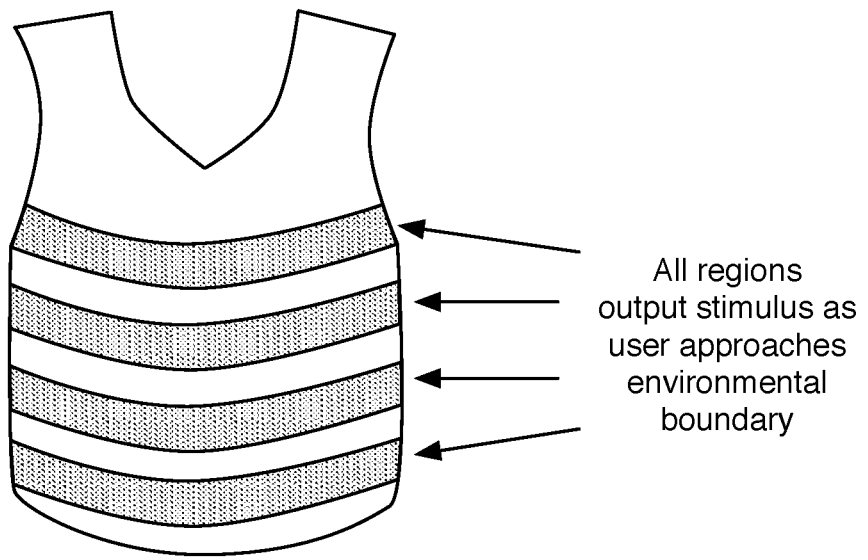
Figure 4D:
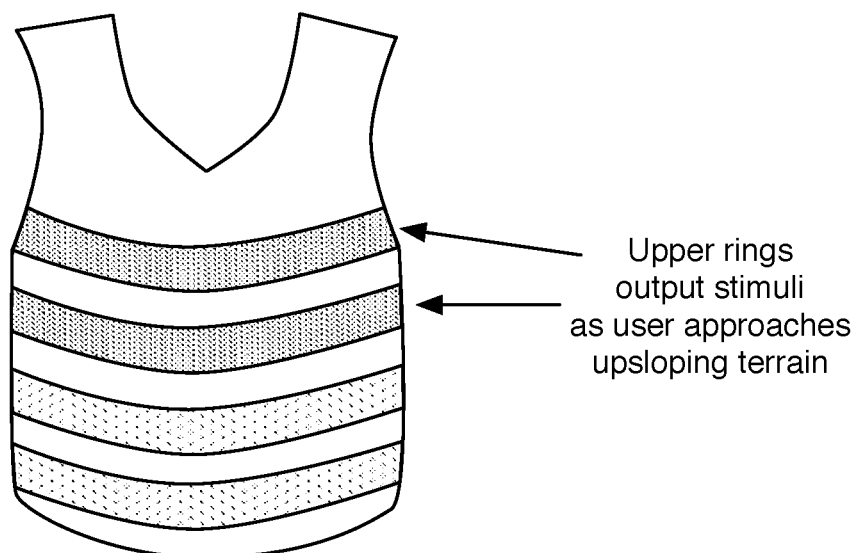

In variations related to feature sets described in Block S120 above, the transformation model can additionally or alternatively transform, encode, or otherwise associate aspects of the third feature set with complex or combined outputs of the array of tactile interface devices, and/or other outputs of devices coupled to the user or otherwise able to communicate with the user. In variations, the transformation operation can result in generation of encodings related to both subdomains and stimulus outputs available using the array of tactile stimulus devices. For instance, in relation to environmental boundaries (e.g., walls), the transformation model can produce encodings for subdomains of the array of tactile interface devices that are associated with environmental boundaries, and output amplitudes of the stimuli provided by those subdomains can be increased as the user moves toward the environmental boundaries. In a specific example, in a device variation that has a distribution of the array of tactile stimulation devices configured in a set of rings about the torso of the user (e.g., with the array coupled to an upper garment): as the user moves forward toward a wall, all of the anterior tactile stimulation devices across all rings can be used to indicate that the user is approaching the wall, wherein amplitudes or intensities of stimuli provided increase as the user gets closer to the wall, an example of which is shown in FIG. 4C. In another example, as the user moves toward upsloping terrain, stimulation devices across upper rings can be used to indicate that the user is entering a region of upsloping terrain (wherein the number of rings used corresponds to the grade of the terrain), an example of which is shown in FIG. 4D.

Figure 7D:
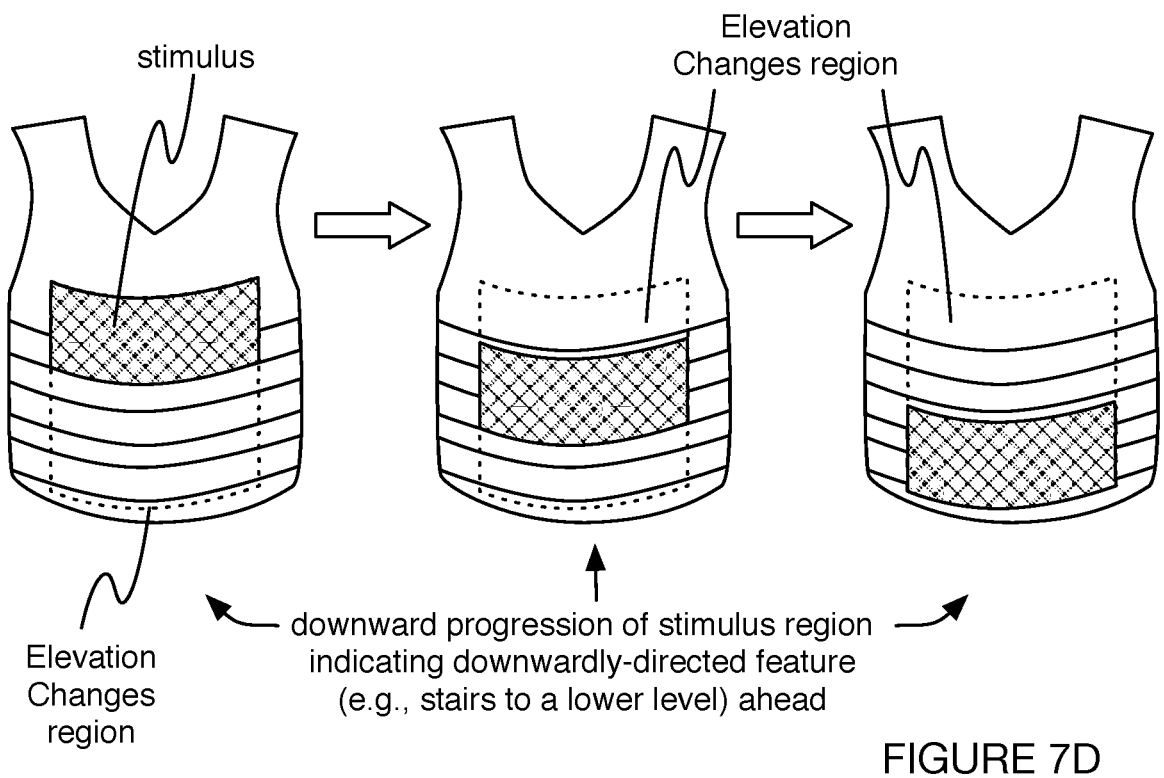

In another example, Block S130 can include generating encodings that result in outputs that sweep across a subdomain of the array of tactile interface devices and/or generates other spatial phenomena. Such sweeping behavior can correspond to, in examples, environmental features involving elevation change (e.g., sloping terrain, staircases, etc.; wherein the sweep is directed according to the direction of elevation change, such as shown in FIG. 7D), velocity and/or direction of a moving object (e.g., object moving near the user, such as in front of the user), and/or any other suitable phenomena. In a specific example (e.g., as shown in FIGS. 7A and 7D), the sensory output device includes a region associated with elevation changes (e.g., same region as one or more of the bands described above; partially or fully overlapping one or more of the bands; entirely separate from the bands; all or substantially all of the sensory output actuators of the device; etc.). The elevation changes region can include one or more vertical strips, rectangular areas, and/or any other suitable shapes. Based on an elevation change feature, the elevation changes region can be controlled to output a sweeping phenomenon, wherein progressive subsets of the actuators of the region are activated over time. For example, based on a downward elevation change feature, the sweeping phenomenon can include activating an upper subset of actuators (e.g., in a vertical strip), then an upper-middle subset, then a middle subset, then a lower-middle subset, then a lower subset, then optionally repeating the sweeping phenomenon (e.g., starting again beginning with the upper subset). The subsets of the elevation changes region can be overlapping, adjacent, separated by a non-zero space, and/or have any other suitable arrangement. The subsets can be substantially equivalent in size and/or shape, and/or can be different from each other. However, the sweeping behavior can additionally or alternatively be generated in any other suitable manner.

Additionally or alternatively, such spatial phenomena can include rotating outputs (e.g., wherein outputs are provided in a circular motion, such as circle defining a substantially horizontal normal axis and/or an axis substantially normal a ring subdomain axis), such as outputs rotating about a central position (e.g., position determined as described above, such as a position on a ring corresponding to the object classification, with an angular position corresponding to the object heading). Such rotating outputs can correspond to, for example, rotating and/or rotatable objects (e.g., revolving door, potentially-harmful spinning obstacle, etc.). However, variations of these examples can be conducted in any other suitable manner, and/or Block S130 can additionally or alternatively include generating encodings corresponding to any other suitable spatial phenomena.

Block S140 recites: selecting a subset of the set of output parameters (e.g., the subset corresponding to information of interest to the user, which functions to implement a reduction operation to provide a subportion of available information to the user). Block S140 preferably functions to allow a user or other entity to receive content in a customized manner. In variations, Block S140 can include receiving an input, provided by the user or another entity, wherein the input includes a selection of types of information that the user would like to be provided with, through the array of tactile interface devices. Block S140 can additionally or alternatively automatically filter the types of information that the user will be provided with through the array of tactile interface devices, based upon characterizations of the user (e.g., characterizations of the user's impairments, characterizations of the user's demographics, characterizations of the user's interests, etc.).

In a first example, the user may opt to receive information related to objects below knee height, given a tendency for injuries related to objects below a threshold height. In a second example, the user may opt to receive information pertaining to objects in his/her peripheral vision, due to a vision impairment related to peripheral vision lost. In a third example, the user may opt to receive color-related information, due to a degree of color blindness. In a fourth example, the user may opt to receive distance information, due to a vision impairment related to depth perception. However, in Block Sly, any other suitable filter can be applied, with respect to information provided to the user through the array of tactile interface devices.

Block S150 recites: controlling a sensory output system to generate outputs based on the output (e.g., executing control signals operable to deliver the subset of the set of output parameters with the distribution of tactile interface devices coupled to the user). Block S150 functions to enable outputs to be delivered to the user through the tactile interface devices, according to the transformation and encoding algorithms of Blocks S120-S140. The control signals can be executed according to methods described in U.S. application Ser. No. 14/750,626, titled "Providing Information to a User Through Somatosensory Feedback"; however, the control signals can additionally or alternatively be executed in any other suitable manner. For instance, Block S150 can include receiving one or more user inputs operable to adjust a gain level (or other aspect) of output stimuli, such that the user can customize the "strength" of stimuli provided through the array of tactile interface devices.

Block S160 recites: repeating any or all of Blocks S110-S150 (e.g., as the user and/or surrounding objects moves about the environment). Block S160 functions to provide real-time or near real time information updates to the user, such that the user is provided with current information through alternative sensory modes as the user interacts with his/her environment. Block S160 is preferably performed in near real time, such that information provided to the user has no perceptible lag, and the user can move about his/her environment while receiving up-to-date information. Block S160 can include repeating Blocks S120-S150 at a desired frequency (e.g., per unit time). Additionally or alternatively, Block S160 can include repeating Blocks S120-S150 based on any suitable trigger. For instance, Block S160 can include repeating Blocks S120-S150 based on motion of the user (e.g., using motion detecting sensors, such as accelerometers, gyroscopes, etc.), such that repetition is based on motion of the user without the environment. Additionally or alternatively, Block S160 can be implemented in any other suitable manner.

Figure 8:
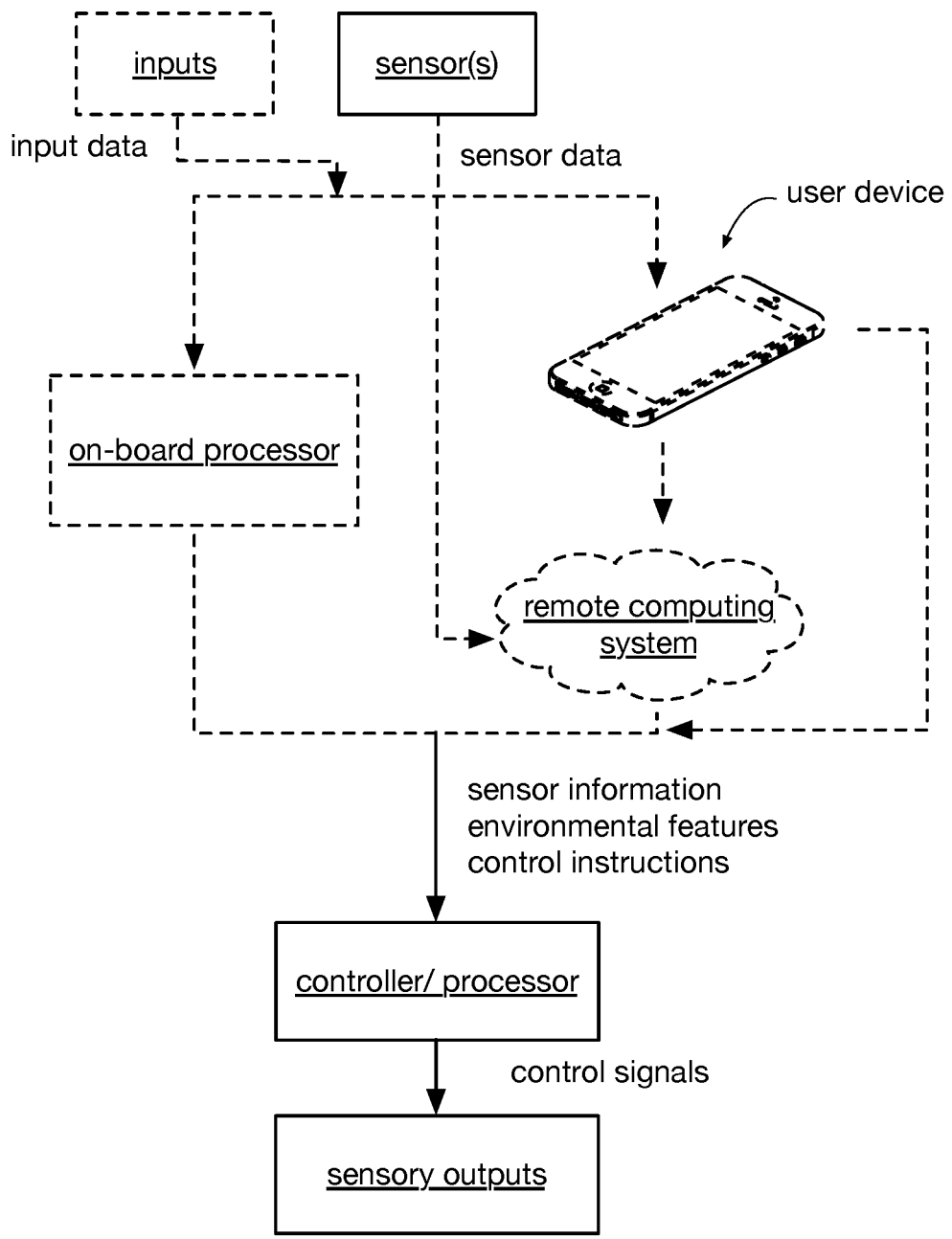
FIG. 8 depicts examples of optional data flows between components of the system.

Any or all elements of the method can be performed by any elements of the system, and/or by any other suitable elements. In one example, a first portion of the method (e.g., Block S110) is performed by one or more sensors (e.g., distinct from the sensory output device, integrated with the sensory output device), electronic user devices (e.g., smart phones), and/or remote computing systems, and a second portion of the method (e.g., Block S120 and optionally Block S130) is performed by one or more computing devices distinct from the sensory output device (e.g., the remote computing systems, electronic user devices, etc.), wherein the results of which (e.g., environmental information, feature sets, output parameters, sensory output device operation instructions, etc.) are transmitted (e.g., wirelessly) to the sensory output device, whereupon the sensory output device performs a third portion of the method (e.g., the remaining elements not performed in the first and second portions) based on the information included in the transmission (example shown in FIG. 8). In a second example, Block S110 is performed by one or more sensors (e.g., distinct from the sensory output device, integrated with the sensory output device), electronic user devices (e.g., smart phones), and/or remote computing systems, and the results (e.g., environmental information) are transmitted (e.g., wirelessly) to the sensory output device, whereupon the sensory output device performs all other elements of the method based on the information included in the transmission (example shown in FIG. 8). However, the elements of the method can additionally or alternatively be distributed between devices in any other suitable manner, or can be performed by a single device.

Furthermore, the method 100 can include any other suitable Blocks operable to promote provision of information to the user, through an array of tactile interface devices, in any other suitable manner.

An alternative embodiment preferably implements the some or all of above methods in a computer-readable medium storing computer-readable instructions. The instructions are preferably executed by computer-executable components preferably integrated with a communication routing system. The communication routing system may include a communication system, routing system and a pricing system. The computer-readable medium may be stored on any suitable computer readable media such as RAMs, ROMs, flash memory, EEPROMs, optical devices (CD or DVD), hard drives, floppy drives, or any suitable device. The computer-executable component is preferably a processor but the instructions may alternatively or additionally be executed by any suitable dedicated hardware device.

Although omitted for conciseness, embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A method for providing information to a user, the method comprising:
   determining a first position of a first object relative to the user, wherein determining the first position comprises, at a first sensor mechanically coupled to the user, sampling a first measurement indicative of the first position;
   determining a second position of a second object relative to the user, wherein determining the second position comprises:
      determining a user location and a user orientation of the user;
      at a second sensor not mechanically coupled to the user, sampling a second measurement indicative of a location of the second object; and
      based on the location, the user location, and the user orientation, determining the second position; and
   at a tactile output device mechanically coupled to the user, the tactile output device comprising: a first plurality of tactile actuators defining a first band; and a second plurality of tactile actuators defining a second band distinct from the first band:
      based on the first position, determining a first set of control instructions for the first plurality of tactile actuators, comprising: selecting a first tactile actuator of the first plurality such that the first object is closer to the first tactile actuator than to any other tactile actuator of the first plurality;

in response to determining the first set of control instructions, controlling the first plurality of tactile actuators based on the first set of control instructions, comprising controlling the first tactile actuator to actuate;

based on the second position, determining a second set of control instructions for the second plurality of tactile actuators, comprising: selecting a second tactile actuator of the second plurality such that the second object is closer to the second tactile actuator than to any other tactile actuator of the second plurality; and substantially concurrent with controlling the first plurality of tactile actuators based on the first set of control instructions, in response to determining the second set of control instructions: controlling the second plurality of tactile actuators based on the second set of control instructions, comprising controlling the second tactile actuator to actuate.

2. The method of claim 1, further comprising:

determining that the user is moving toward a bottom of a staircase;

in response to determining that the user is moving toward the bottom of the staircase, at the tactile output device, determining a third set of control instructions for a third plurality of tactile actuators, wherein the third plurality of tactile actuators comprises:
  a lower set of actuators;
  a middle set of actuators arranged above the lower set; and
  an upper set of actuators arranged above the middle set; and in response to determining the third set of control instructions, controlling the third plurality of tactile actuators based on the third set of control instructions, comprising:
  controlling the lower set of actuators to actuate;
  after controlling the lower set of actuators, controlling the middle set of actuators to actuate; and
  after controlling the middle set of actuators, controlling the upper set of actuators to actuate.

3. The method of claim 2, wherein the upper, middle, and lower sets of actuators cooperatively define a region intersecting the first band and the second band.

4. The method of claim 1, wherein the first sensor comprises an optical sensor.

5. The method of claim 1, wherein:
the first object is an inanimate object; and
the second object is a person mechanically coupled to a user device comprising the second sensor.

6. The method of claim 5, further comprising, before controlling the second plurality of tactile actuators based on the second set of control instructions:
determining, based on social graph information, that the person is associated with the user.

7. The method of claim 1, further comprising:
classifying the first object as an obstacle type;
based on classifying the first object as the obstacle type, associating the first object with the first band, wherein the first set of control instructions are determined in response to associating the first object with the first band;
classifying the second object as a person type; and
based on classifying the second object as the person type, associating the second object with the second band,
wherein the second set of control instructions are determined in response to associating the second object with the second band.

8. The method of claim 7, further comprising:
determining a third position of a third object relative to the user;
classifying the third object as the obstacle type; and
based on classifying the third object as the obstacle type, associating the third object with the first band;
wherein:
determining the first set of control instructions for the first plurality of tactile actuators further comprises: based on the third position and on associating the third object with the first band, selecting a third tactile actuator of the first plurality such that the third object is closer to the third tactile actuator than to any other tactile actuator of the first plurality; and
controlling the first plurality of tactile actuators based on the first set of control instructions further comprises: substantially concurrent with controlling the first tactile actuator to actuate, controlling the third tactile actuator to actuate.

9. The method of claim 8, wherein:
a first object distance between the first position and the user is greater than a third object distance between the third position and the user;
based on the first object distance, the first tactile actuator is controlled to actuate at a first actuator intensity; and
based on the third object distance, the third tactile actuator is controlled to actuate at a third actuator intensity greater than the first actuator intensity.

10. The method of claim 1, wherein:
while controlling the first plurality of tactile actuators, a third tactile actuator of the second plurality does not actuate, wherein the first object is closer to the third tactile actuator than to any other tactile actuator of the second plurality; and
while controlling the second plurality of tactile actuators, a fourth tactile actuator of the first plurality does not actuate, wherein the second object is closer to the fourth tactile actuator than to any other tactile actuator of the first plurality.

11. The method of claim 1, wherein:
the tactile output device comprises a garment encircling a body part of the user, the body part defining a longitudinal axis;
the first band substantially encircles the body part;
the second band substantially encircles the body part; and
the first band is displaced from the second band along the longitudinal axis.

12. The method of claim 11, wherein:
the body part is a torso; and
the tactile output device further comprises an array of tactile actuators substantially encircling the torso, wherein the array comprises the first and second pluralities of tactile actuators.

13. A method for providing information to a user, the method comprising:
determining a first position of a first object relative to the user;
determining a second position of a second object relative to the user; and
at a tactile output device mechanically coupled to the user, the tactile output device comprising: a first plurality of tactile actuators defining a first band; and a second plurality of tactile actuators defining a second band distinct from the first band:

based on the first position, determining a first set of control instructions for the first plurality of tactile actuators, comprising: selecting a first tactile actuator of the first plurality such that the first object is closer to the first tactile actuator than to any other tactile actuator of the first plurality;

in response to determining the first set of control instructions, controlling the first plurality of tactile actuators based on the first set of control instructions, comprising controlling the first tactile actuator to actuate;

based on the second position, determining a second set of control instructions for the second plurality of tactile actuators, comprising: selecting a second tactile actuator of the second plurality such that the second object is closer to the second tactile actuator than to any other tactile actuator of the second plurality;

substantially concurrent with controlling the first plurality of tactile actuators based on the first set of control instructions, in response to determining the second set of control instructions: controlling the second plurality of tactile actuators based on the second set of control instructions, comprising controlling the second tactile actuator to actuate;

determining that the user is moving toward a bottom of a staircase;

in response to determining that the user is moving toward the bottom of the staircase, at the tactile output device, determining a third set of control instructions for a third plurality of tactile actuators, wherein the third plurality of tactile actuators comprises:
a lower set of actuators;
a middle set of actuators arranged above the lower set; and
an upper set of actuators arranged above the middle set; and in response to determining the third set of control instructions, controlling the third plurality of tactile actuators based on the third set of control instructions, comprising:
controlling the lower set of actuators to actuate;
after controlling the lower set of actuators, controlling the middle set of actuators to actuate; and
after controlling the middle set of actuators, controlling the upper set of actuators to actuate.

14. A method for providing information to a user, the method comprising:

determining a first position of a first object relative to the user;

classifying the first object as an obstacle type;

determining a second position of a second object relative to the user;

classifying the second object as a person type; and at a tactile output device mechanically coupled to the user, the tactile output device comprising: a first plurality of tactile actuators defining a first band; and a second plurality of tactile actuators defining a second band distinct from the first band:

based on classifying the first object as the obstacle type, associating the first object with the first band;

based on classifying the second object as the person type, associating the second object with the second band;

in response to associating the first object with the first band and based on the first position, determining a first set of control instructions for the first plurality of tactile actuators, comprising: selecting a first tactile actuator of the first plurality such that the first object is closer to the first tactile actuator than to any other tactile actuator of the first plurality;

in response to determining the first set of control instructions, controlling the first plurality of tactile actuators based on the first set of control instructions, comprising controlling the first tactile actuator to actuate;

in response to associating the second object with the second band and based on the second position, determining a second set of control instructions for the second plurality of tactile actuators, comprising: selecting a second tactile actuator of the second plurality such that the second object is closer to the second tactile actuator than to any other tactile actuator of the second plurality; and substantially concurrent with controlling the first plurality of tactile actuators based on the first set of control instructions, in response to determining the second set of control instructions: controlling the second plurality of tactile actuators based on the second set of control instructions, comprising controlling the second tactile actuator to actuate.

\* \* \* \* \*